United States Patent
Carballo et al.

(10) Patent No.: US 11,839,583 B1
(45) Date of Patent: Dec. 12, 2023

(54) APPARATUS AND METHOD FOR REDUCTION OF NEUROLOGICAL MOVEMENT DISORDER SYMPTOMS USING WEARABLE DEVICE

(71) Applicant: Encora, Inc., Boston, MA (US)

(72) Inventors: Daniel Carballo, Cambridge, MA (US); Kyle Pina, Boston, MA (US); Allison Davanzo, Boston, MA (US); Trang Luu, Cambridge, MA (US)

(73) Assignee: ENCORA, INC., Boston, MA (US)

( * ) Notice: Subject to any disclaimer, the term of this patent is extended or adjusted under 35 U.S.C. 154(b) by 317 days.

(21) Appl. No.: 16/563,087

(22) Filed: Sep. 6, 2019

Related U.S. Application Data

(60) Provisional application No. 62/797,310, filed on Jan. 27, 2019, provisional application No. 62/729,977, filed on Sep. 11, 2018.

(51) Int. Cl.
    *A61H 23/00* (2006.01)
    *A61H 23/02* (2006.01)
    (Continued)

(52) U.S. Cl.
    CPC ............ *A61H 23/02* (2013.01); *A61B 5/1101* (2013.01); *A61B 5/112* (2013.01); *A61B 5/4082* (2013.01);
    (Continued)

(58) Field of Classification Search
    CPC ..... A61B 5/4082; A61B 5/681; A61B 5/1101; A61B 5/112; A61H 2201/1635;
    (Continued)

(56) References Cited

U.S. PATENT DOCUMENTS 4,842,607 A * 6/1989 Repperger ............ A61F 5/0118
    244/230
6,458,089 B1 * 10/2002 Ziv-Av ................. A61B 5/1101
    600/595
(Continued)

FOREIGN PATENT DOCUMENTS

| CA | 2716407 C | 4/2018 |
|---|---|---|
| CN | 204426918 U | 7/2015 |

(Continued)

OTHER PUBLICATIONS

Beasley et al., "An Overview of Genetic Algorithms: Part 1, Fundamentals", University Computing, 15(2), pp. 58-69, 1993.
(Continued)

*Primary Examiner* — Philip R Wiest
*Assistant Examiner* — Tyler A Raubenstraw
(74) *Attorney, Agent, or Firm* — Goodwin Procter LLP

(57) ABSTRACT

A multimodal wearable band which uses mechanical vibrations to stimulate sensory neurons in the wrist or ankle in order to reduce the severity of tremors, rigidity, involuntary muscle contractions, and bradykinesia caused by neurological movement disorders and to free users from freezing induced by movement disorders. The device uses sensors to provide output used by a processing unit to determine the optimal stimulation pattern for each user and to determine when stimulation is necessary, and then uses one or more vibration motors to accordingly stimulate the user's neurological pathways to lessen the severity of a user's symptoms. The device can also be adapted to integrate with 3rd party devices.

13 Claims, 18 Drawing Sheets

(51) Int. Cl.
*A61B 5/11* (2006.01)
*A61B 5/00* (2006.01)

(52) U.S. Cl.
CPC ........ *A61B 5/681* (2013.01); *A61H 2201/165* (2013.01); *A61H 2201/1635* (2013.01); *A61H 2201/5007* (2013.01); *A61H 2201/5025* (2013.01); *A61H 2230/085* (2013.01); *A61H 2230/625* (2013.01)

(58) Field of Classification Search
CPC .............. A61H 23/02; A61H 2201/165; A61H 2201/5007; A61H 2201/5025; A61H 2230/085; A61H 2230/625; A61H 2201/5058; A61H 2230/00; A61H 2201/50; A61H 2201/5005; A61H 2230/60
See application file for complete search history.

(56) References Cited

U.S. PATENT DOCUMENTS

| | | | |
|---|---|---|---|
| 6,695,794 B2 | 2/2004 | Kaiser et al. | |
| 6,730,049 B2 | 5/2004 | Kalvert | |
| 6,959,215 B2 | 10/2005 | Gliner et al. | |
| 7,349,739 B2 | 3/2008 | Harry et al. | |
| 7,412,428 B2 | 8/2008 | Nugent | |
| 7,481,782 B2 | 1/2009 | Scott et al. | |
| 8,025,632 B2 | 9/2011 | Einarsson | |
| 8,187,209 B1 | 5/2012 | Giuffrida | |
| 8,190,251 B2 | 5/2012 | Molnar et al. | |
| 8,463,378 B2 | 6/2013 | Tass | |
| 8,644,938 B2 | 2/2014 | Craggs | |
| 8,679,038 B1 | 3/2014 | Giuffrida | |
| 8,744,587 B2 | 6/2014 | Miesel et al. | |
| 8,762,065 B2 | 6/2014 | DiLorenzo | |
| 9,072,891 B1 | 7/2015 | Rao | |
| 9,211,417 B2 | 12/2015 | Heldman et al. | |
| 9,238,142 B2 | 1/2016 | Heldman et al. | |
| 9,282,928 B1 | 3/2016 | Giffrida | |
| 9,289,603 B1 | 3/2016 | Giuffrida et al. | |
| 9,301,712 B2 | 4/2016 | McNames et al. | |
| 9,452,287 B2 | 9/2016 | Rosenbluth et al. | |
| 9,486,389 B2 | 11/2016 | Tass | |
| 9,553,625 B2 | 1/2017 | Hatanaka et al. | |
| 9,616,234 B2 | 4/2017 | Harry et al. | |
| 9,802,041 B2 | 10/2017 | Wong et al. | |
| 9,855,110 B2 | 1/2018 | Bitan et al. | |
| 9,861,283 B1 | 1/2018 | Giuffrida | |
| 9,877,679 B1 | 1/2018 | Giuffrida | |
| 9,877,680 B1 | 1/2018 | Giuffrida et al. | |
| 9,924,899 B2 | 3/2018 | Pracar et al. | |
| 9,936,899 B2 | 4/2018 | Goldman | |
| 9,973,614 B2 | 5/2018 | Thorn et al. | |
| 9,974,478 B1 | 5/2018 | Brokaw et al. | |
| 10,004,901 B2 | 6/2018 | Gliner | |
| 10,016,606 B2 | 7/2018 | Afshar et al. | |
| 10,085,689 B1 | 10/2018 | Giuffrida et al. | |
| 10,092,754 B1 | 10/2018 | Heldman et al. | |
| 10,143,618 B2 * | 12/2018 | Cambridge | A61H 19/32 |
| 10,173,060 B2 | 1/2019 | Wong et al. | |
| 10,179,238 B2 | 1/2019 | Wong et al. | |
| 10,350,410 B2 | 7/2019 | Tass et al. | |
| 10,365,614 B2 | 7/2019 | Von Allmen | |
| 10,426,369 B2 | 10/2019 | Marks | |
| 10,463,141 B2 | 11/2019 | Fitzgerald et al. | |
| 10,478,626 B1 | 11/2019 | Heldman et al. | |
| 10,485,478 B1 * | 11/2019 | Mirov | H02J 7/025 |
| 10,549,093 B2 | 2/2020 | Wong et al. | |
| 10,561,839 B2 | 2/2020 | Wong et al. | |
| 10,603,482 B2 | 3/2020 | Hamner et al. | |
| 10,625,074 B2 | 4/2020 | Rosenbluth et al. | |
| 10,694,992 B1 | 6/2020 | Giuffrida et al. | |
| 10,744,324 B2 | 8/2020 | Ó Laighin et al. | |
| 10,750,946 B1 | 8/2020 | Giuffrida | |
| 10,765,856 B2 | 9/2020 | Wong et al. | |
| 10,786,200 B1 | 9/2020 | Giuffrida | |
| 10,786,625 B1 | 9/2020 | Giuffrida et al. | |
| 10,814,130 B2 | 10/2020 | Wong et al. | |
| 10,820,819 B2 | 11/2020 | Afshar et al. | |
| 10,850,090 B2 | 12/2020 | Rosenbluth et al. | |
| 10,881,856 B2 | 1/2021 | Heldman et al. | |
| 10,905,879 B2 | 2/2021 | Wong et al. | |
| 10,960,207 B2 | 3/2021 | Wong et al. | |
| 10,966,652 B1 | 4/2021 | Giuffrida et al. | |
| 10,974,049 B1 | 4/2021 | Heldman et al. | |
| 11,000,229 B2 | 5/2021 | Leavitt et al. | |
| 11,026,484 B2 | 6/2021 | Perkins et al. | |
| 11,040,198 B1 | 6/2021 | Giuffrida et al. | |
| 11,040,203 B1 | 6/2021 | Giuffrida et al. | |
| 11,058,320 B2 | 7/2021 | Meftah et al. | |
| 11,191,967 B1 | 12/2021 | Giuffrida et al. | |
| 11,191,968 B1 | 12/2021 | Giuffrida et al. | |
| 11,194,888 B1 | 12/2021 | Murphy et al. | |
| 11,253,424 B2 | 2/2022 | Tass et al. | |
| 11,311,235 B1 | 4/2022 | Giuffrida et al. | |
| 11,331,480 B2 | 5/2022 | Hamner et al. | |
| 11,344,722 B2 | 5/2022 | Wong et al. | |
| 11,395,784 B2 | 7/2022 | Molina trejo | |
| 2002/0107556 A1 | 8/2002 | Mcloul et al. | |
| 2003/0006357 A1 * | 1/2003 | Kaiser | A61H 23/02 248/550 |
| 2005/0234309 A1 | 10/2005 | Klapper | |
| 2007/0004570 A1 | 1/2007 | Afanasenko et al. | |
| 2007/0073361 A1 | 3/2007 | Goren et al. | |
| 2007/0203435 A1 | 8/2007 | Novak | |
| 2007/0203533 A1 | 8/2007 | Goren et al. | |
| 2007/0250134 A1 | 10/2007 | Miesel et al. | |
| 2007/0299374 A1 * | 12/2007 | Gesotti | A61H 23/02 601/72 |
| 2008/0053253 A1 * | 3/2008 | Moore | A61B 5/1038 73/865.4 |
| 2009/0024062 A1 | 1/2009 | Einarsson | |
| 2009/0024065 A1 | 1/2009 | Einarsson | |
| 2009/0082691 A1 * | 3/2009 | Denison | A61B 5/30 600/544 |
| 2009/0247910 A1 | 10/2009 | Klapper | |
| 2010/0030119 A1 | 2/2010 | McNames et al. | |
| 2010/0069798 A1 | 3/2010 | Cheng et al. | |
| 2010/0234182 A1 | 9/2010 | Hoffman et al. | |
| 2010/0249637 A1 | 9/2010 | Walter et al. | |
| 2012/0172682 A1 * | 7/2012 | Linderman | G06F 3/015 600/300 |
| 2013/0214913 A1 | 8/2013 | Efrati | |
| 2014/0005743 A1 | 1/2014 | Giuffrida et al. | |
| 2014/0052275 A1 | 2/2014 | Pathak | |
| 2014/0074179 A1 * | 3/2014 | Heldman | G16H 50/50 607/45 |
| 2014/0074180 A1 | 3/2014 | Heldman et al. | |
| 2014/0194781 A1 | 7/2014 | Einarsson | |
| 2014/0336722 A1 | 11/2014 | Rocon De Lima et al. | |
| 2014/0350436 A1 * | 11/2014 | Nathan | A61B 5/1118 600/595 |
| 2014/0375470 A1 | 12/2014 | Malveaux | |
| 2015/0073310 A1 | 3/2015 | Pracar et al. | |
| 2015/0164377 A1 | 6/2015 | Nathan et al. | |
| 2015/0182160 A1 * | 7/2015 | Kim | A61B 5/7475 600/301 |
| 2015/0223731 A1 | 8/2015 | Sahin | |
| 2015/0335521 A1 | 11/2015 | Tedim Ramos Cruz et al. | |
| 2016/0313174 A1 * | 10/2016 | Lightstone | A63B 24/0062 |
| 2017/0007168 A1 | 1/2017 | Mirelman et al. | |
| 2017/0014625 A1 | 1/2017 | Rosenbluth et al. | |
| 2018/0000685 A1 * | 1/2018 | Maloney | A61N 1/0456 |
| 2018/0021576 A1 | 1/2018 | Wong et al. | |
| 2018/0035943 A1 * | 2/2018 | Shemesh | A61B 5/7203 |
| 2018/0036535 A1 | 2/2018 | Wong et al. | |
| 2018/0064344 A1 * | 3/2018 | Nguyen | A61B 5/4836 |
| 2018/0070840 A1 * | 3/2018 | Cronin | A61B 5/7435 |
| 2018/0108241 A1 | 4/2018 | Wong et al. | |
| 2018/0140842 A1 | 5/2018 | OLaighin | |
| 2018/0169400 A1 | 6/2018 | Wong et al. | |
| 2018/0192946 A1 * | 7/2018 | Adachi | A61B 5/022 |

(56) References Cited

U.S. PATENT DOCUMENTS

| | | |
|---|---|---|
| 2018/0203482 A1 | 7/2018 | Nazzaro et al. |
| 2018/0264263 A1 | 9/2018 | Rosenbluth |
| 2018/0266820 A1 | 9/2018 | de Panisse et al. |
| 2018/0289309 A1* | 10/2018 | Chen ................. A61B 5/067 |
| 2018/0296154 A1 | 10/2018 | Johnson et al. |
| 2018/0304082 A1 | 10/2018 | Afshar et al. |
| 2018/0356890 A1* | 12/2018 | Zhang ............... A61H 23/0263 |
| 2018/0361153 A1 | 12/2018 | Heldman et al. |
| 2018/0369064 A1* | 12/2018 | Baxter ................. A61F 7/02 |
| 2019/0001121 A1* | 1/2019 | Lara .................. A61B 5/374 |
| 2019/0001129 A1 | 1/2019 | Rosenbluth et al. |
| 2019/0038222 A1* | 2/2019 | Krimon ............... A61B 5/1107 |
| 2019/0059733 A1 | 2/2019 | Nguyen |
| 2019/0110949 A1* | 4/2019 | Bhatti .................. A61H 23/02 |
| 2019/0110950 A1* | 4/2019 | Smith .................. G06F 1/163 |
| 2019/0143098 A1 | 5/2019 | Kaplan et al. |
| 2019/0183724 A1 | 6/2019 | Sifferlin |
| 2019/0209022 A1* | 7/2019 | Sobol ................. A61B 5/0022 |
| 2019/0298605 A1* | 10/2019 | Rabolt ............... A61H 23/0263 |
| 2019/0365286 A1* | 12/2019 | Powers, III .......... A61B 5/6828 |
| 2020/0054889 A1 | 2/2020 | Makansi |
| 2020/0061378 A1 | 2/2020 | Ganguly et al. |
| 2020/0093400 A1 | 3/2020 | Hamner et al. |
| 2020/0163588 A1 | 5/2020 | Prevost et al. |
| 2020/0179151 A1 | 6/2020 | Negretto et al. |
| 2020/0179687 A1 | 6/2020 | Wong et al. |
| 2020/0188210 A1 | 6/2020 | Molina Trejo |
| 2020/0188223 A1 | 6/2020 | Nguyen |
| 2020/0289814 A1 | 9/2020 | Hamner et al. |
| 2020/0338358 A1 | 10/2020 | Makansi |
| 2020/0410893 A1 | 12/2020 | Ridington |
| 2021/0007874 A1 | 1/2021 | Galiana Bujanda et al. |
| 2021/0030613 A1 | 2/2021 | Kodama et al. |
| 2021/0045957 A1* | 2/2021 | Fuhrer ................ A61H 1/0288 |
| 2021/0052883 A1 | 2/2021 | Wong et al. |
| 2021/0085976 A1 | 3/2021 | Heldman et al. |
| 2021/0100999 A1 | 4/2021 | Rosenbluth et al. |
| 2021/0113152 A1 | 4/2021 | Turner |
| 2021/0113834 A1 | 4/2021 | Wong et al. |
| 2021/0186794 A1 | 6/2021 | Seim et al. |
| 2021/0244316 A1 | 8/2021 | Khaled |
| 2021/0244940 A1 | 8/2021 | Liberatore et al. |
| 2021/0252278 A1 | 8/2021 | Hamner et al. |
| 2021/0283400 A1 | 9/2021 | Hamner et al. |
| 2021/0308460 A1 | 10/2021 | Wong et al. |
| 2021/0330547 A1 | 10/2021 | Moaddeb et al. |
| 2021/0330974 A1 | 10/2021 | Wong et al. |
| 2021/0379374 A1 | 12/2021 | Hamner et al. |
| 2021/0401664 A1 | 12/2021 | Tass |
| 2021/0402172 A1 | 12/2021 | Ross et al. |
| 2022/0007994 A1 | 1/2022 | Mattioli |
| 2022/0008786 A1 | 1/2022 | Shah |
| 2022/0165413 A1 | 5/2022 | Murphy et al. |
| 2022/0266011 A1 | 8/2022 | Wong et al. |
| 2022/0266012 A1 | 8/2022 | Hamner et al. |

FOREIGN PATENT DOCUMENTS

| | | | |
|---|---|---|---|
| CN | 106178261 A | 12/2016 | |
| CN | 206424425 U | 8/2017 | |
| CN | 107307933 A | 11/2017 | |
| WO | WO-2019046180 A1 * | 3/2019 | ........... A61H 1/0285 |

OTHER PUBLICATIONS

Buki et al., "Vib-bracelet: A Passive Absorber for Attenuating Forearm Tremor", Med Biol Eng Comput, vol. 56, pp. 923-930, 2018.

Conrad et al., "Effects of Wrist Tendon Vibration on Arm Tracking in People Poststroke", J. Neurophysiol., 106(3), pp. 1480-1488, Jun. 2011.

Conrad et al., "Effect of Tendon Vibration on Hemiparetic Arm Stability in Unstable Workspaces", PLOS one, 10(12), pp. 1-18, Dec. 2015.

Deisenroth et al., "A Survey on Policy Search for Robotics", Foundations and Trends in Robotics, vol. 2(1-2) pp. 1-141, 2013.

Gebai et al., "Parkinson's Disease Treatment as Seen from a Mechanical Point of View", Advances in Parkinson's Disease, 5, pp. 97-106, Nov. 2016.

Hagbarth et al., "The Effects of Muscle Vibration in Spasticity, Rigidity, and Cerebellar Disorders", J. Neurol. Neurosurg. Pshyciat., vol. 31, pp. 207-213, 1968.

Lora-Millan et al., "Mechanical Vibration does not Systematically Reduce the Tremor in Essential Tremor Patients", vioRxiv 398875, http://dx.doi.org/10.1101/398875, pp. 1-35, Aug. 2018.

Macerollo et al., "Effect of Vibration on Motor Performance: A new intervention to improve bradykinesia in Parkinson's disease?", MDS Abstracts, 2 pages, Jun. 2016.

Turkistani, "Development of an Effective Portable and Flexible Glove for Hand Tremor Suppression", Master's Theses, 65 pages, Spring, 2017.

European Patent Office; International Search Report and Written Opinion dated Jan. 27, 2022 for PCT Application No. PCT/US2021/053561 (19 pages).

* cited by examiner

APPARATUS AND METHOD FOR REDUCTION OF NEUROLOGICAL MOVEMENT DISORDER SYMPTOMS USING WEARABLE DEVICE

PRIORITY

This patent application claims the benefit of U.S. provisional patent application 62/729,977, filed on Sep. 11, 2018, and U.S. provisional patent application 62/797,310, filed on Jan. 27, 2019. These applications are hereby incorporated, in their entirety, by reference.

TECHNICAL FIELD

The present invention relates to wearable medical devices and in particular to wearable medical devices that mitigate symptoms of neurological movement disorders.

BACKGROUND ART

There are a number of neurological movement disorders which exhibit a range of somewhat similar symptoms, examples of which follow. Essential tremor is characterized by tremor of the extremities. Parkinson's Disease (PD) can cause tremor, rigidity, bradykinesia, and temporary freezing or inability to begin a motion. Restless Leg Syndrome does not cause a tremor; however, it causes a strong compulsion to move and shake the patient's legs. Tremor can also be present as a side effect of certain medications.

There are approximately 10 million people living with Parkinson's Disease (PD) in the world today, and over 70% of these patients experience tremors—the involuntary trembling or shaking of the extremities. Other symptoms of PD include stiffness or rigidity of the muscles, bradykinesia (defined as slowness of movement), and freezing (defined as the temporary, involuntary inability to move).

Parkinson's Disease has no cure. Treatments at the moment consist of medications to address patients' symptoms, though these do not reverse the effects of the disease. Patients often take a variety of medications at different doses and different times of day to manage symptoms. PD medications are most often dopaminergic, either supplying or mimicking the effects of dopamine to replenish the depleted dopamine state caused by the disease.

Surgical procedures can be prescribed for patients who have exhausted their medical treatment options. The first method of surgical treatment is Deep Brain Stimulation (DBS). In this procedure, electrodes are inserted into the brain, and then an impulse generator battery is implanted under the collar bone or in the abdomen. The patient uses a controller to power the device on or off, as needed, to help control tremors. DBS can be effective for both Parkinson's disease and essential tremor, but this procedure is incredibly invasive and expensive.

The second surgical procedure available for Parkinson's patients is Duopa therapy. Duopa therapy requires a small hole (a stoma) to be surgically made in the stomach to place a tube in the intestine. Duopa, which is similar to normal PD medications taken through pills, is then pumped directly into the intestine, which improves absorption and reduces off-times of medications taken by pill.

A similar disorder, called essential tremor, has an even higher incidence rate with an estimated 100 million cases worldwide. These tremors can get bad enough that patients no longer have the ability to cut their food, tie their shoes, or sign their name. Essential tremor medications can include beta blockers and anti-seizure medications. These medications are known to cause fatigue, heart problems, and nausea.

Restless Leg Syndrome (RLS) affects roughly 10% of the population in the United States. RLS can also be a side effect of primary Parkinson's Disease. RLS is characterized by unpleasant tingling sensations in the patient's legs. These sensations occur when the legs are still and are alleviated when the legs are in motion. As a result, RLS patients are compelled to move or shake their legs. This is particularly detrimental to the quality of patients' sleep as they are unable to remain still.

RLS is commonly treated by dietary changes, medications, and/or physical therapy. Dietary changes can include eliminating caffeine, alcohol, and tobacco. Medications prescribed for RLS can include the same type of medications prescribed for Parkinson's Disease (such as dopamine agonists and carbidopa-levodopa) and benzodiazepines (such as lorazepam, Xanax, Valium, and Ativan). Physical therapy for RLS can include massaging the legs or electrical or vibrational stimulation.

One example of a device that uses vibration to treat RLS is described in "Systems, devices, and methods for treating restless leg syndrome and periodic limb movement disorder," Walter, T. J., & Marar, U. (2010), U.S. Patent Application Publication No. US20100249637A1. This device is a lower leg sleeve with sensors and actuators, but it does not store or transmit data, nor does it address any of the other symptoms common to neurological movement disorders.

There are also a number of pharmaceutical avenues for the management of neurological movement disorder that function by promoting dopamine, a chemical produced by the brain which helps control body movement. This chemical is lacking in the brains of patients with diseases such as Parkinson's disease. Pharmaceutical treatment for Parkinson's disease is expensive, costing users thousands of dollars annually; ineffective, wearing off quickly; and thought to actually accelerate neurodegeneration.

There also exists an injection-based Botox treatment for more severe tremors which costs tens of thousands of dollars annually and works by killing the nerves responsible for the tremors. This is effective in reducing the tremors, but the death of the nerves also causes a significant decrease in mobility. Additionally, this treatment is only available at very specialized treatment centers and therefore is not an option for the vast majority of patients.

There are a number of devices that attempt to control unwanted movement using surface-based treatment, but none have proven to be completely non-invasive and effective. Many have settled on electrical stimulation as their chosen mode of neurostimulation for the relief of unwanted movement. This can involve various equipment and inconvenient procedures such as gel pads or electrodes that require shaving for proper attachment. See "Closed-loop feedback-driven neuromodulation," DiLorenzo, D. J. (2014), U.S. Pat. No. 8,762,065B2. These devices only work after the electrical treatment is concluded, and the effects have not been shown to last for extended periods of time, leading to the assumption that many of these inconvenient treatments must be administered throughout the day to maintain tremor reduction. See "Devices and methods for controlling tremor," Rosenbluth, K. H., Delp, S. L., Paderi, J., Rajasekhar, V., & Altman, T. (2016), U.S. Pat. No. 9,452,287B2; "Systems for peripheral nerve stimulation to treat tremor," Wong, S. H., Rosenbluth, K. H., Hamner, S., Chidester, P., Delp, S. L., Sanger, T. D., & Klein, D. (2017), U.S. Pat. No. 9,802,041B2. The aforementioned treatment poses significant risk for patients with pacemakers, and has also been found to cause skin irritation. They provide benefit only for tremor and do not provide relief from other symptoms of neurological movement disorders, such as bradykinesia, freezing of gait, dystonia, or involuntary or compulsive rhythmic movement.

Perhaps the most relevant studies have emerged in the last few years and demonstrate that using vibration may improve motor performance. It seems that there is much variation in efficacy, which depends on the frequency of vibration, as well as the patient's condition. Macerollo et al. demonstrated that 80 Hz peripheral tactile vibration may result in less slowing and a decrease in repetitive hand movement in "Effect of Vibration on Motor Performance: A new Intervention to Improve Bradykinesia in Parkinson's Disease?", Macerollo A, et al., (2016), Neurology April 2016, 86 (16 Supplement) P5.366. For post-stroke patients, 70 Hz has proven effective. This is demonstrated by Conrad M O, et al., in two separate papers: "Effects of wrist tendon vibration on arm tracking in people poststroke," Conrad M O, Scheidt R A, Schmit B D (2011), J Neurophysiol, 2011; 106(3): 1480-8; and "Effect of Tendon Vibration on Hemiparetic Arm Stability in Unstable Workspaces," Conrad M O, Gadhoke B, Scheidt R A, Schmit B D (2015), PLoS ONE 10(12): e0144377. Even paretic muscles are proven to respond to frequencies between 150 and 160 Hz, and the effects of such vibration are seen in a lasting reduction in weakness and spasticity in the treated muscles. See "The effects of muscle vibration in spasticity, rigidity, and cerebellar disorders," Hagbarth, K. E., & Eklund, G. (1968), Journal of neurology, neurosurgery, and psychiatry, 31(3), 207-13. There exists one device which provides haptic signals around a user's wrist using actuators positioned along a band. These actuators slide along the band to change location relative to one another in order to provide signals in the correct location. See "Wearble device," Zhang, Haiyan, Helmes, John Franciscus Marie, Villar, Nicolas (2018), U.S. Patent No. US20180356890A1.

Therefore, there is a need for a device that non-invasively, reliably, and affordably relieves symptoms of neurological movement disorders.

SUMMARY OF THE EMBODIMENTS

In accordance with one embodiment of the invention, a wearable device for mitigating a movement disorder of a subject. The device includes an attachment system configured to be attached to a body part of a subject. The device further includes a set of body part sensors to provide a set of sensor outputs related to a body part parameter. The device also includes a processing unit operationally coupled to the set of body part sensors. The processing unit is configured to quantify an extent or characteristic of the movement disorder based on the set of sensor outputs. The device further includes a set of mechanical transducers operationally coupled to the processing unit to provide a set of mechanical outputs. The processing unit is further configured to control the set of mechanical outputs of the set of mechanical transducers so as to mitigate an extent of the movement disorder through a feedback loop.

Optionally, the attachment system includes a wristband, and the mechanical transducers are distributed throughout the circumference of the wristband. Optionally, the device is operated by a button on a face of the device, the button is configured on the face to allow for ease of use by a patient whose fine motor control is affected by a neurological movement disorder. Optionally, the wristband is configured with a hook-and-loop fastener, such that the wristband can be fastened with a single hand for ease of use by those whose fine motor control is affected by a neurological movement disorder. Optionally, the device further includes a battery that can be coupled to a magnetically aligned charging cable for charging the device, which provides ease of use by a patient whose fine motor control is affected by a neurological movement disorder.

Optionally, the device is configured to be fully autonomous, using passive movement disorder sensing to initiate active operation. Optionally, the processing unit is further configured to use closed loop control, along with a state machine, to address symptoms. Optionally, the processing unit is further configured to control the mechanical transducers, without requiring control inputs from external control units. Optionally, the processing unit is further configured to collect and store data.

Optionally, the symptoms are selected from the group consisting of tremor, rigidity, bradykinesia, compulsion to move, and combinations thereof. Optionally, the processing unit is further configured to detect a freezing gait of a patient with Parkinson's Disease. Alternatively or additionally, the processing unit is further configured to control the set of mechanical transducers so as to relieve freezing gait of a patient with Parkinson's Disease.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

Figure 1:
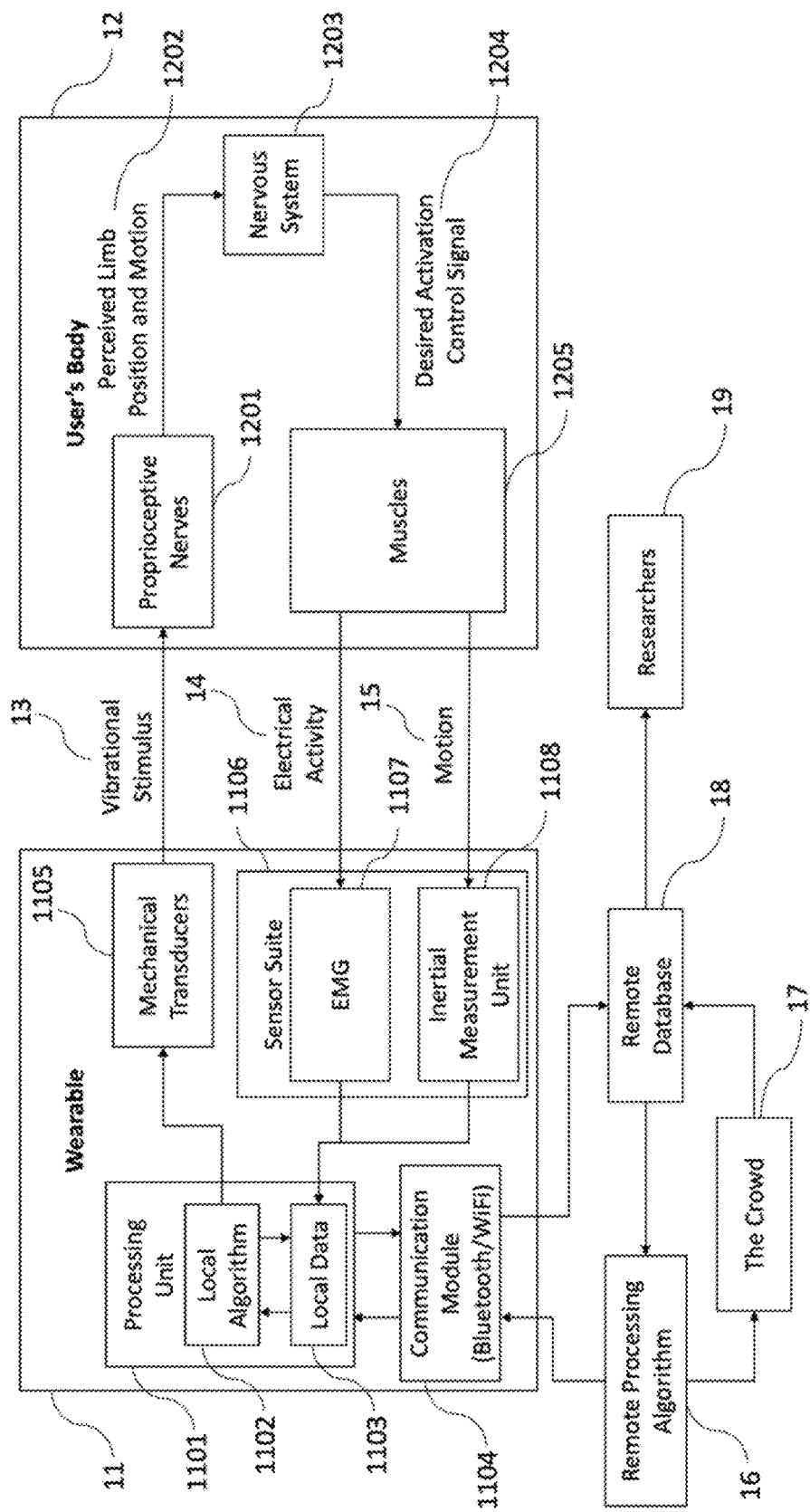
FIG. 1 illustrates a system for mitigating movement disorder in accordance with an embodiment of the present invention.

Definitions. As used in this description and the accompanying claims, the following terms shall have the meanings indicated, unless the context otherwise requires:

A "set" includes at least one member.

A "body part" is a part of a human body, such as a limb (examples of which include an arm, a leg, an ankle, and a wrist) or the neck.

A "body part sensor" is a sensor responsive to a parameter, associated with a body part, the parameter selected from the group consisting of force, motion, position, EMG signal directed to a set of muscles of the body part and combinations thereof.

A "mechanical transducer" is a device having an electrical input and a mechanical output configured to provide physical stimulation to a subject.

A "movement disorder sensor" is a sensor that is configured to provide a measurement associated with a neurological movement disorder.

An "attachment system" is a system or a device having a means to mechanically affix component subsystems to the user's person.

A "housing" is a primary enclosed casing which contains one or more component subsystems.

A "band" is a flexible segment of material which encircles a body part or portion of a body part for the purpose of affixment which may also house one or more component subsystems.

The term "vibrational stimulus" refers to a vibration or series of vibrations produced by a vibration motor or group of vibration motors embedded in the device. These vibrations are used to stimulate a response from the targeted proprioceptors in the user's body.

The term "stimulation pattern" refers to a vibrational stimulus which is characterized by a number of parameters including frequency, amplitude, and waveform. A "stimulation pattern" can also refer to a longer time scale behavior over which the above-mentioned parameters evolve over time.

The term "proprioception" refers to the sense of the position of one's own limbs or body parts and the intensity of force being applied through that body part. A proprioceptor is a sensory neuron which is used for proprioception. There are two types of proprioceptors: "muscle spindles" which are located in the muscle and the "Golgi tendon organs" which are located in the tendons.

The term "neurological movement disorder" refers to any of the neurological conditions that cause abnormally increased or decreased movements which may be voluntary or involuntary. These include but are not limited to: Ataxia, cervical dystonia, chorea, dystonia, functional movement disorder, Huntington's disease, multiple system atrophy (MSA), paresis, hemiparesis, quadriparesis, post-stroke movement disorders, myoclonus, Parkinson's disease (PD), Parkinsonism, drug induced Parkinsonism (DIP), progressive supranuclear palsy (PSP), restless legs syndrome (RLS), tardive dyskinesia, Tourette syndrome, spasticity, rigidity, bradykinesia, tremor, essential tremor (ET), alcohol or drug withdrawal induced tremor, drug induced tremor, psychogenic tremor, rest tremor, action tremor, cerebellar lesion, rubral tremor, isometric tremor, task-specific tremor, orthostatic tremor, intention tremor, postural tremor, periodic limb movement disorder, and Wilson's disease.

The term "training period" refers to a period or phase of the device's operation during which the device is conducting experimentation or collecting and analyzing data for the purpose of deducing the optimal stimulation pattern.

The present invention is directed generally towards wearable medical devices and in particular towards the mitigation of tremors, rigidity, bradykinesia, involuntary rhythmic movements, and freezing associated with neurological movement disorders through mechanical vibrational stimulation of the tendon bundles in the wrist and autonomous sensing, feedback, and adjustment. There are also a number of considerations taken into the embodiment of the device which facilitate ease of use by the disabled populations for whom the invention is intended, including integration with 3rd party devices.

Embodiments of the present invention include systems and methods of treating symptoms of neurological movement disorders by stimulating proprioceptors. In some embodiments, the systems are wearable devices. In some embodiments, the systems and methods can be used for any neurological movement disorder, including but not limited to Parkinson's Disease, Essential Tremor, post-stroke movement disorders, or Restless Leg Syndrome. In some embodiment, the symptoms treated include tremor, rigidity, bradykinesia, stiffness, hemiparesis, and freezing. In some embodiments, the symptoms treated include muscle contraction caused by dystonia. In some embodiments, the symptoms treated include the inability to locate one's limbs in space. In some embodiments, the proprioceptors targeted for stimulation are located in the wrist. In some embodiments, the proprioceptors targeted for stimulation are located in the ankle. In some embodiments, the proprioceptors targeted for stimulation are located in the neck.

In some embodiments, the systems provide stimulus to the proprioceptive nerves (proprioceptors) for reducing symptoms by the use of vibration motors positioned around the surface of the wrist In some embodiments, the systems cycle through frequency patterns and waveforms of stimulation to find the pattern that results in the greatest reduction of movement disorder symptoms. In some embodiments, the systems use random white-noise subthreshold stimulation in order to leverage the effect of sensory stochastic resonance. In some embodiments, the systems are coupled to one or more sensors that measure the user's tremor for each of a set of possible stimulation patterns, and the systems assign the pattern of stimulation that relates to the biggest measured decrease in tremor amplitude of that user relative to the tremor exhibited in the absence of stimulation In some embodiments, the device finds (learns) the optimal stimulation parameters for use in reducing the symptoms by using sensor-based optimization, including but not limited to model free reinforcement learning, genetic algorithms, Q-learning. These parameters can include any quantities used to define a stimulation waveform such as frequency, amplitude, phase, duty cycle, etc. In some embodiments, these learned parameters also describe the longer time scale behavior of the stimulation pattern evolving over time. In some embodiments, the device determines the optimal stimulation as the weighted average of the optimal stimulations for each of the independent symptoms observed where the weights are proportional to the symptom severity relative to the other observed symptoms. For example, if the patient experienced tremors and rigidity, and the severity of the tremors was double that of the rigidity, the output stimulation would be two times the optimal tremor reducing pattern superposed with one times the optimal rigidity reducing pattern. In some embodiments, the device senses all of the active symptoms and elects to reduce only the symptom with the worst severity. In some embodiments, the device, via sensors, measures the shaking due to RLS of the user and assigns the pattern that relates to the biggest decrease in shaking amplitude of that user where the amplitude is that of the sensor signal and the difference is defined relative to the amplitude observed in the absence of stimulation from the device.

In some embodiments, the sensors coupled to the device are a combination of accelerometers, gyroscopes, IMUS, or other motion-based sensors. In some embodiments, the sensors coupled to the device also include electromyography (EMG) sensors to monitor muscle activation in order to sense tremor severity, rigidity, or movement due to RLS. In some embodiments, the device collects data on the characteristics of the user's symptoms, such as motion amplitude and frequency or muscle activity with sensors contained in the device such as an accelerometer, pressure sensors, force sensors, gyroscope, Inertial Measurement Unit (IMU), or electromyography (EMG) sensors. In some embodiments, the above-mentioned data would be stored through storage components contained within the device. In some embodiments, the above-mentioned data is regularly consolidated for the purpose of larger scale data analysis through a wired or wireless transfer of data to a larger storage location not on the device.

In some embodiments, the actuators are resistive heating elements rather than vibration motors. In some embodiments, the actuators are vibration motors. In some embodiments, the actuators are electromagnets. In some embodiments, the actuators are electropermanent magnets. In some embodiments, the actuators are piezoelectric actuators. In some embodiments, the actuators are voice coil vibration motors. In some embodiments, the actuators are rotating eccentric mass vibration motors. In some embodiments, the device is an accessory band to a third-party smartwatch or other wearable computing device. In some embodiments, the device can connect wirelessly (for example via Bluetooth) to the user's smartphone. In some embodiments, the device can be configured to provide contextualized data about the user's condition. For example, the system can correlate symptom onset or degree with time of day, activity level, medication, diet, other symptoms, etc. In some embodiments, this can be accomplished by transmitting extracted sensor signal features to the user's smartphone. An accompanying smartphone application can periodically prompt the user to input other information like activity level, diet, and medication. The application then logs this data with time matched symptom sensor signal features to be reviewed by the user and/or their physician. In some embodiments, the device can be started by passive sensing of the onset of symptoms such as the on/off phenomenon of Parkinson's patients taking L-dopa. In some embodiments, this can be accomplished by continuously reading sensor data, even while in the "off" state, and then switching to the "on" state when one of the sensor data features, such as amplitude, surpasses a preset threshold value. In some embodiments, the device can be used to amplify an existing but subtle tremor for the purpose of early diagnosis. In some embodiments, this can be accomplished by manually testing a set of stimulation patterns until the tremor is apparent, either visually or as detected by an extracted feature of the sensor data surpassing some preset threshold. In some embodiments, this can be accomplished autonomously by inverting the stimulation selection algorithm heuristic such that it converges to the stimulation pattern which maximizes tremor amplitude as measured by the symptom sensor relative to the tremor amplitude measured in the absence of stimulation from the device.

FIG. 1 illustrates a system for mitigating movement disorder in accordance with an embodiment of the present invention. FIG. 1 shows a wearable device 11 interfacing with a user's body 12. The user's body 12 includes proprioceptive nerves 1201, perceived limb position and motion 1202, a nervous system 1203, desired activation control signal 1204, and muscles 1205. The muscles 1205 output electrical activity 14, which is detected by the EMG sensor 1107 in the wearable's sensor suite 1106, and collected as local data 1103. The muscles 1205 also output motion 15, which is detected by the inertial measurement unit (IMU) 1108. The IMU 1108 measures the body's specific force, angular rate, and orientation, and reports to the processing unit 1101. The processing unit 1101 receives the local data 1103 and executes a local algorithm 1102. Using the local data 1103, the processing unit 110, based on results of the local algorithm 1102, instructs the mechanical transducers 1105 to deliver a specific vibrational stimulus 13. The proprioceptive nerves 1201 detect the vibrational stimulus 13 and send the perceived limb position and motion 1202 to the nervous system 1203. Based on that signal, the nervous system 1203 sends a desired activation control signal 1204 to activate the muscles 1205 in a way that either alters or perpetuates their electrical activity 14 and motion 15. The local data 1103 collected by the sensor suite 1106 continues to be processed by the local algorithm 1102 again, and continues to affect the output of the mechanical transducers 1105. The local data 1103 is also transmitted via the communication module 1104 to a remote processing algorithm 16, and to a remote database 18 for long-term data storage and access by researcher 19. The remote database 18 also receives data from the greater population, or the crowd 17, and sends this data to the remote processing algorithm 16. The remote processing algorithm 16 analyzes the data and returns the results of the analysis both to the processing unit 1101, via the communication module 1104, and also to the crowd 17. In this way, data from the crowd 17 may influence the way that the local algorithm 1102 operates.

Figure 2:
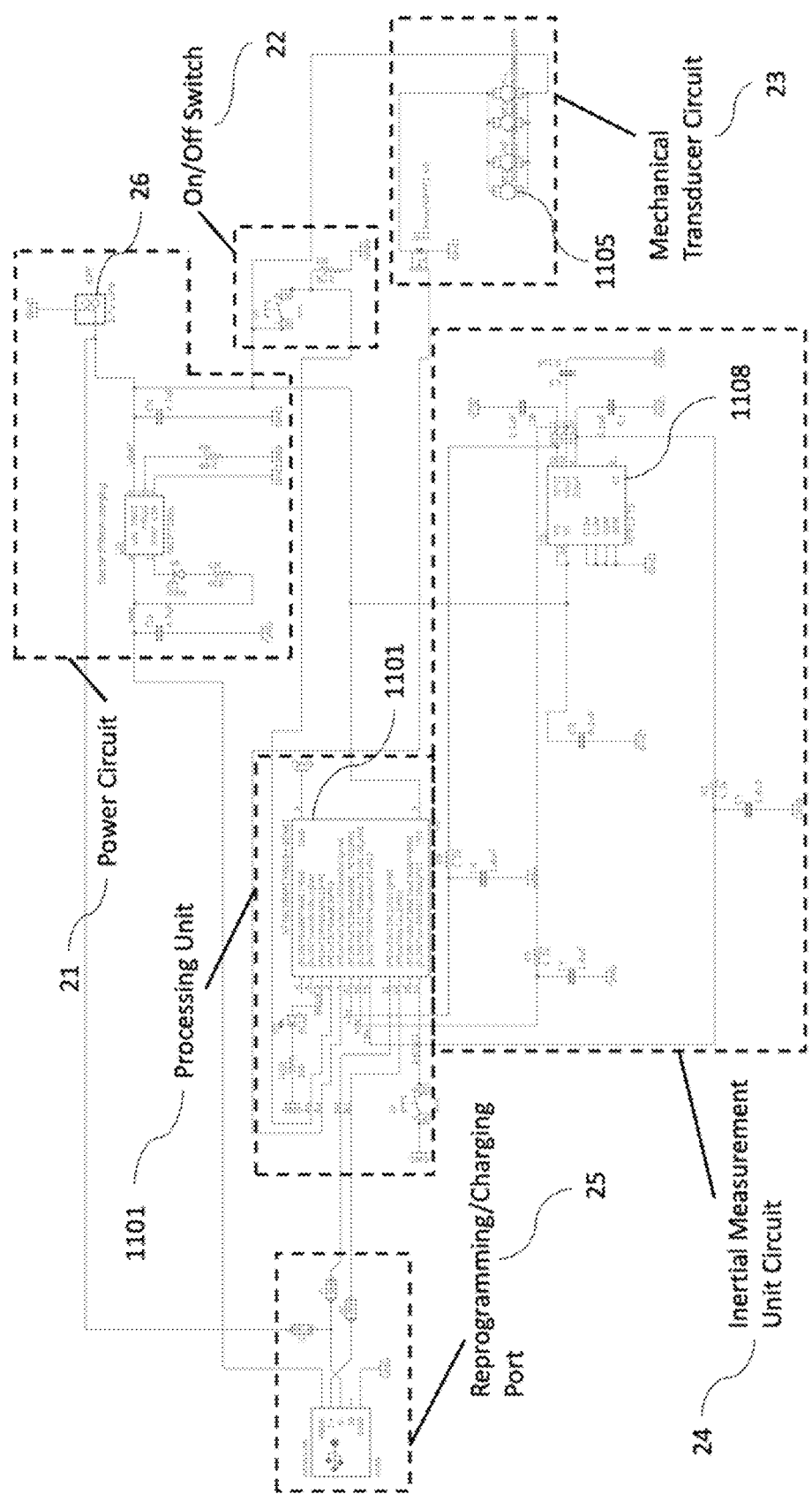
FIG. 2 is an electrical schematic highlighting the main sub-circuits of the system in FIG. 1.

FIG. 2 is an electrical schematic highlighting the main sub-circuits of the system in FIG. 1. FIG. 2 shows the processing unit 1101, which receives tremor vibration data from the inertial measurement unit 1108 in the inertial measurement unit circuit 24. This data is used by the processing unit 1101 to drive the mechanical transducers 1105 in the mechanical transducer circuit 23 at various frequencies and amplitudes. The entire system receives power from a rechargeable battery 26 in the power/charging circuit 21. The reprogramming/charging port 25 can be used to both recharge the battery 26 and reprogram the processing unit 1101. The power is switched on and off via the on/off button 22.

Figure 3:
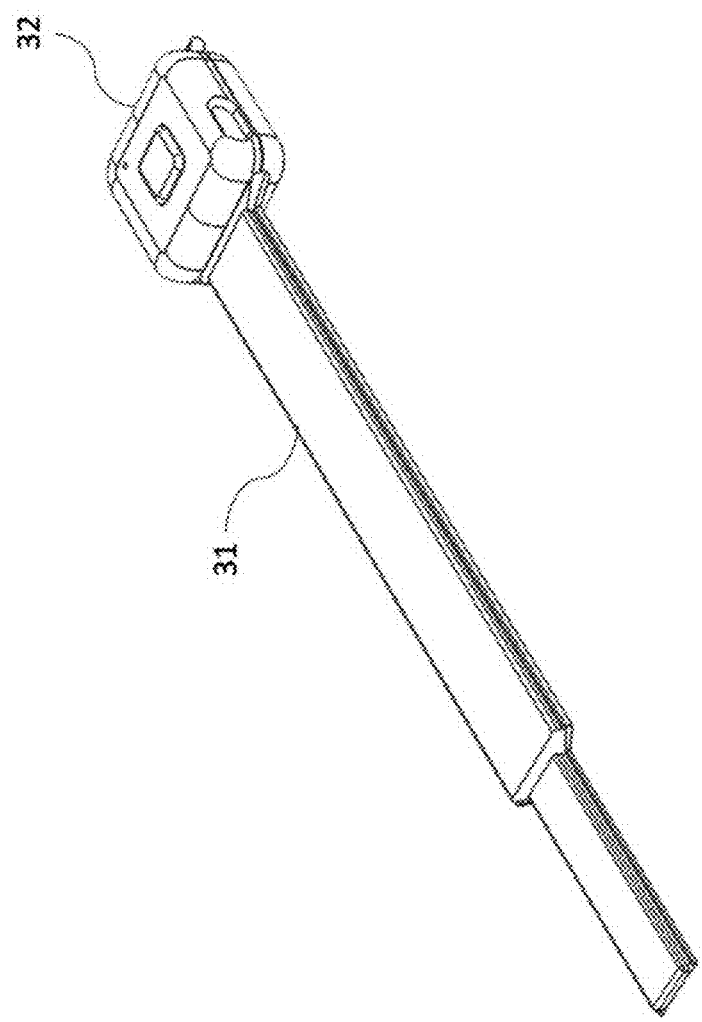
FIG. 3 is an isometric view of a wearable device in accordance with an embodiment of the present invention.

FIG. 3 is an isometric view of a wearable device in accordance with an embodiment of the present invention. FIG. 3 shows the main electronics housing 32 of the device and the band 31 of the device that interfaces with the user's wrist.

Figure 4:
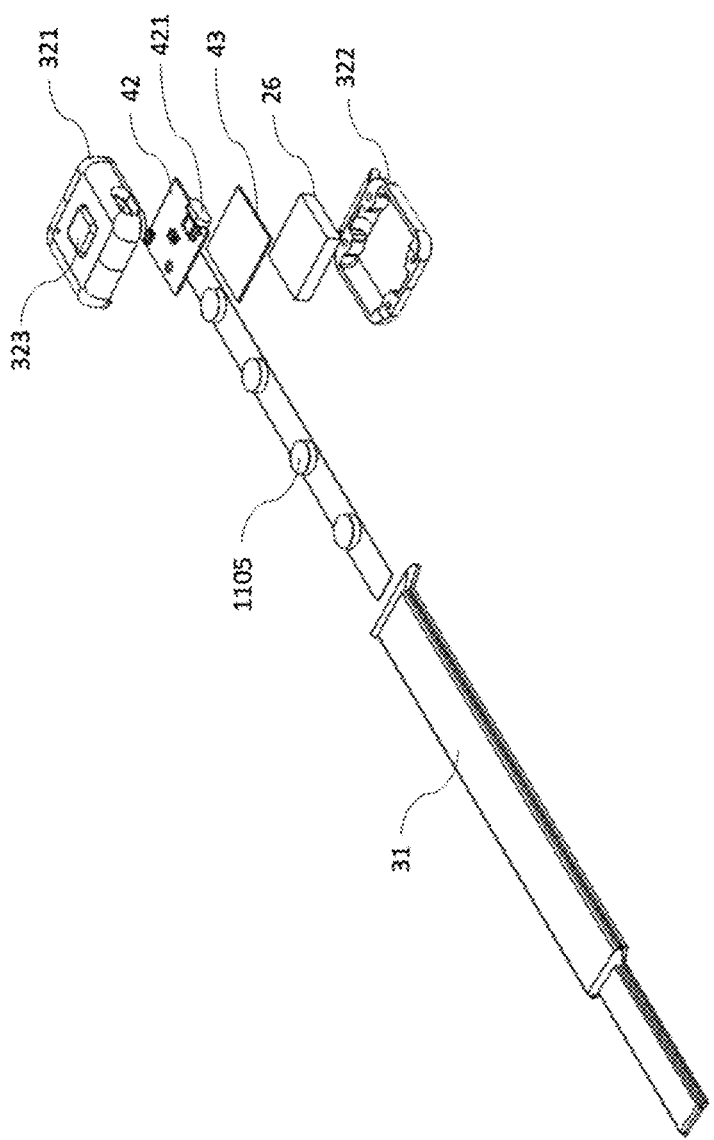
FIG. 4 is an exploded isometric view of a wearable device, in which the vibration motors are housed in the band rather than in the main electronics housing, in accordance with an embodiment of the present invention.

FIG. 4 is an exploded isometric view of a wearable device, in which the vibration motors are housed in the band rather than in the main electronics housing, in accordance with an embodiment of the present invention. The mechanical transducers 1105 are housed in the band 31 which interfaces with the user's wrist. Between the top and bottom halves of the housing 321 322, there is a printed circuit board (PCB) 42, a silicone square to insulate the bottom of the PCB 43, and a rechargeable battery 26. The battery 26 includes protection circuitry to protect from overcharging and unwanted discharging. To recharge the battery 26, a magnetic plug-in head 421 is inserted into the PCB 42. The magnetic plug-in head 421 allows patients who have difficulty performing tasks that require fine motor skills to easily charge the device with a magnetic charging cable. The device is intended to work after the patient turns the device on by pressing the single, large button 323 on top of the electronic housing top 321. The button is provided for ease of use by a patient whose fine motor control is affected by a neurological movement disorder.

Figure 5:
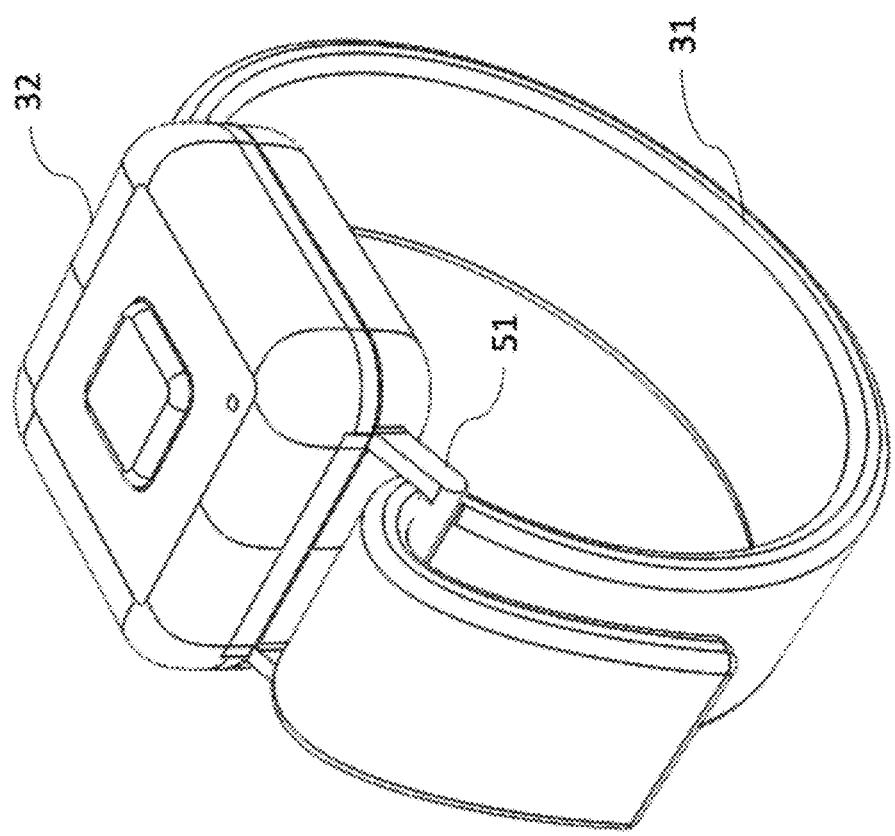
FIG. 5 is an isometric view of a wearable device, in which the device includes a loop mechanism to allow single handed adjustment of the band on the user's wrist, in accordance with an embodiment of the present invention.

FIG. 5 is an isometric view of a wearable device, in which the device includes a loop mechanism 51 to allow single handed adjustment of the band 31 on the user's wrist, in accordance with an embodiment of the present invention. FIG. 5 shows the main electronics housing 32, the band 31 as it looks when worn on the user's wrist, and an adjustment mechanism 51 that is integrated into the main electronics housing 32.

Figure 6:
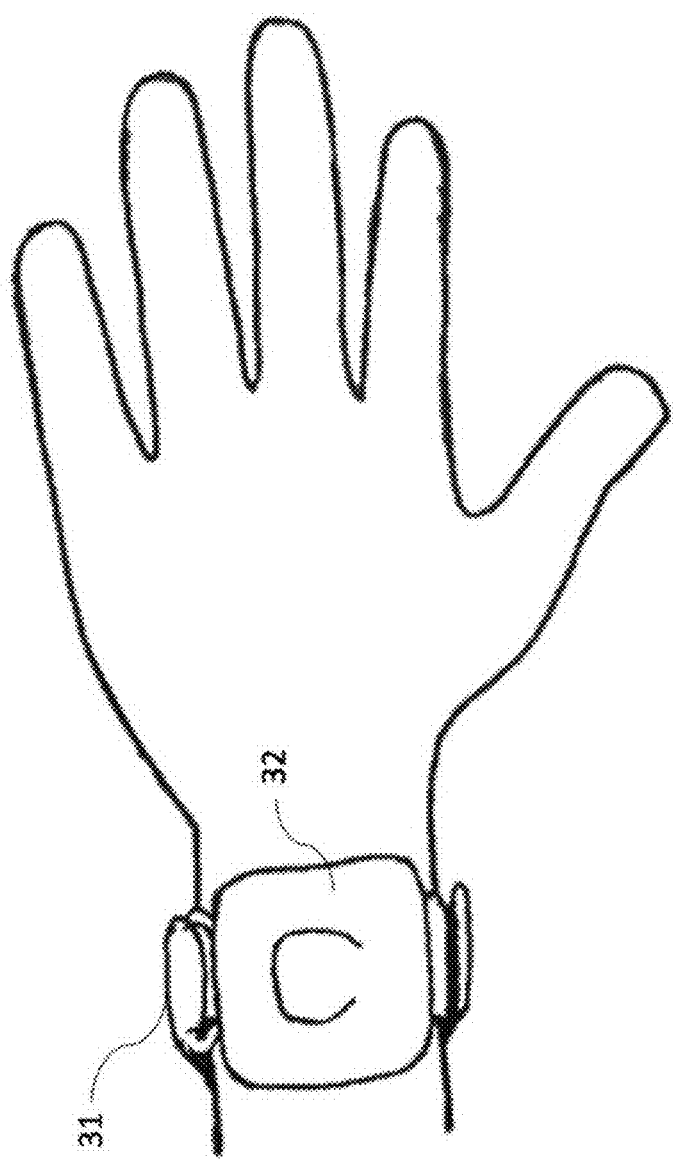
FIG. 6 shows an embodiment of the present invention worn on a hand viewed from above.

FIG. 6 shows an embodiment of the present invention worn on a hand viewed from above. FIG. 6 shows the main electronics housing 32 and the band 31 that interfaces with the user's wrist.

Figure 7:
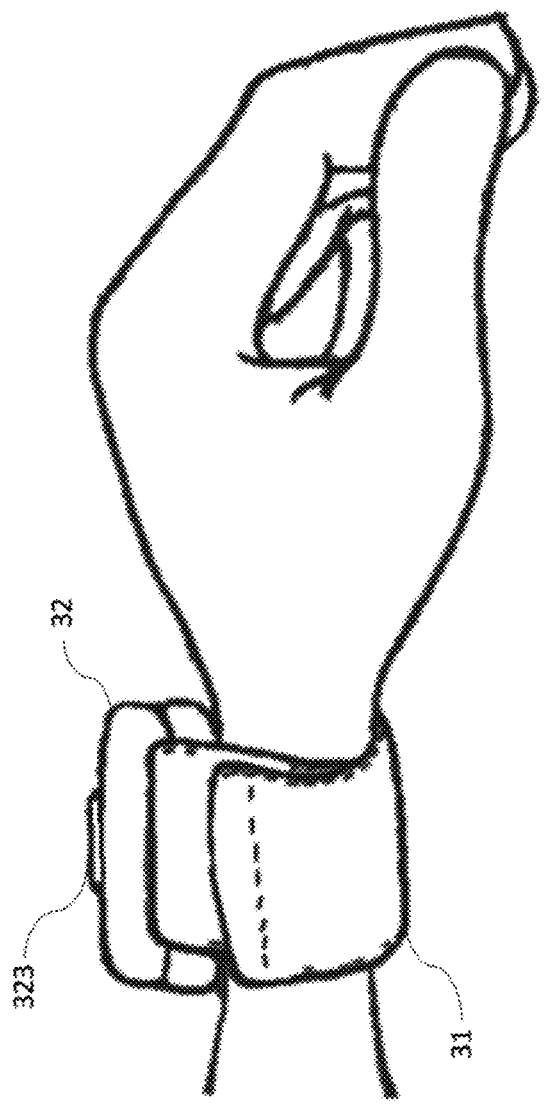
FIG. 7 shows an embodiment of the present invention worn on a hand viewed from the side.

FIG. 7 shows an embodiment of the present invention worn on a hand viewed from the side. FIG. 7 shows the main electronics housing 32, the band 31 that interfaces with the user's wrist, and the on/off button 323 that a patient may use to begin/stop the vibrational stimulation. The on/off button 323 is integrated into the main electronics housing 32.

Figure 8:
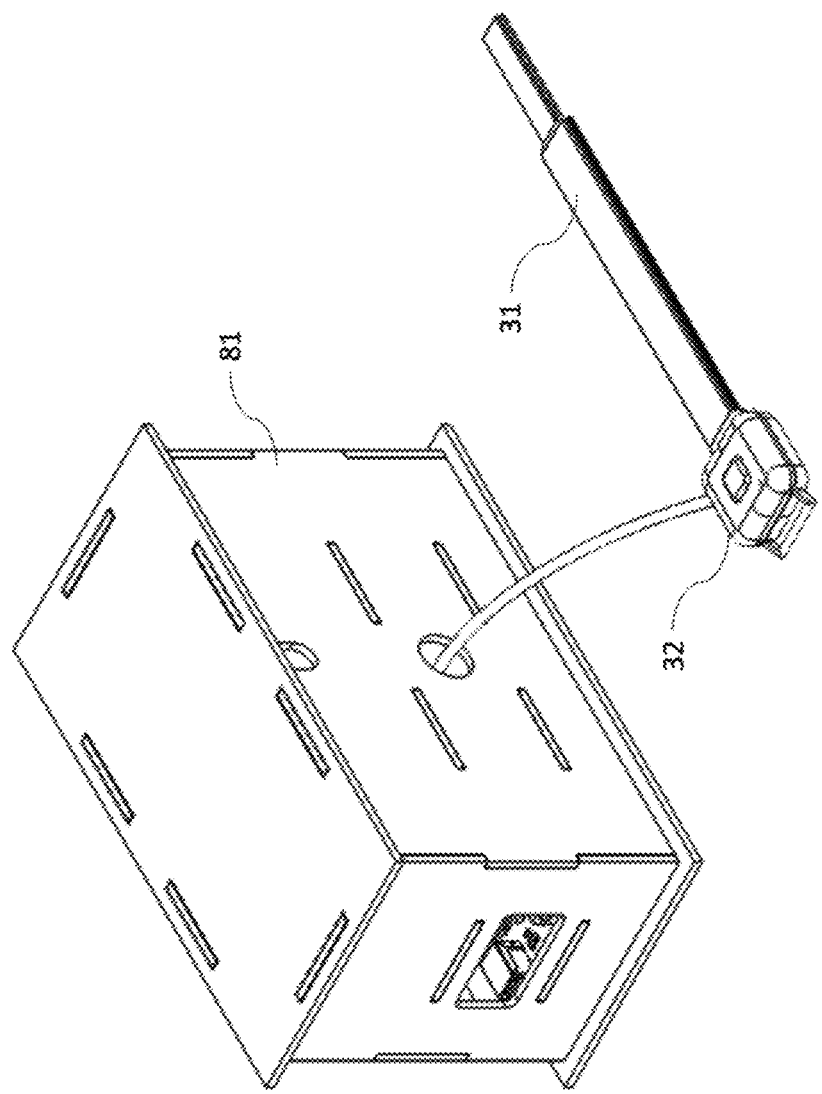
FIG. 8 shows a testing configuration for the wearable medical device, which may be used for more rigorous data collection, in accordance with an embodiment of the present invention.

FIG. 8 shows a testing configuration for the wearable medical device, which may be used for more rigorous data collection, in accordance with an embodiment of the present invention. FIG. 8 shows the main electronics housing 32 and the band 31 that interfaces with the user's wrist. These are connected to a data logging apparatus 81 which collects and stores data. Data can continue to be collected and stored over a larger time scale than on the device alone, as this testing configuration is equipped with a larger processor and storage capacity. At the time of analysis, more complex and computationally heavy data analysis is possible on the collected data stored in the data logging apparatus 81 utilizing the larger processor.

Figure 9:
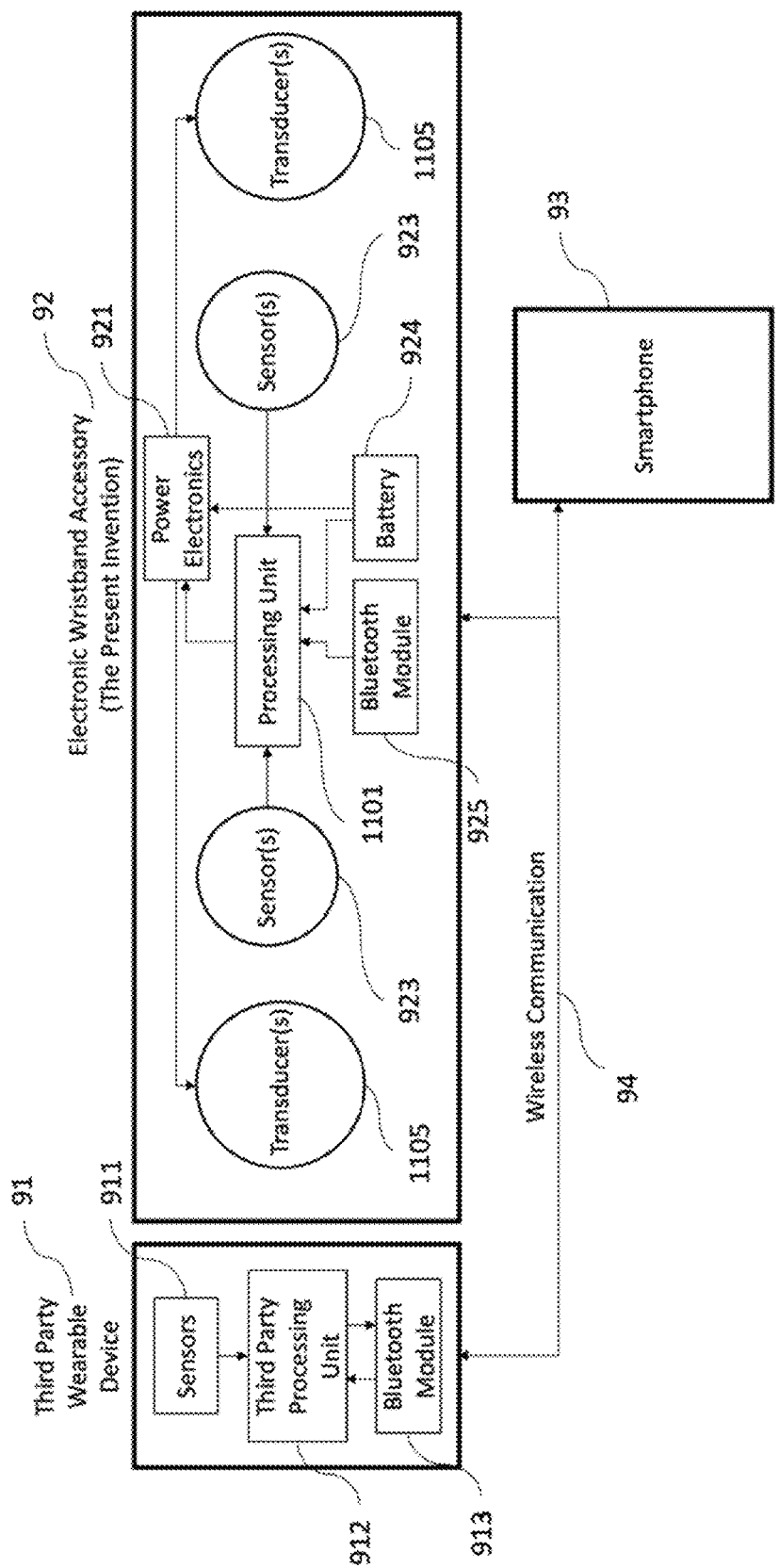
FIG. 9 illustrates a wearable device for mitigating movement disorder, in which the device is an accessory to a third-party smartwatch or other wearable computing device, in accordance with an embodiment of the present invention.

FIG. 9 illustrates a wearable device for mitigating movement disorder, in which the device is an accessory to a third-party smartwatch or other wearable computing device 91, in accordance with an embodiment of the present invention. In such an embodiment, some or all of the computation 912 and sensing 911 are offloaded to the third-party wearable device 91. The third-party device then sends a set of motor commands wirelessly 94 (over Bluetooth for example 913 925) to a processing unit 1101 on the accessory band 92. This processing unit 1101 interfaces with the transducers 1105 on the band to execute the desired motor commands. In this embodiment, the accessory band 92 has its own battery 925. In some embodiments, the band also has its own specialized sensors 923 (such as electromyography sensors), the signals of which are communicated to the third-party processing unit 912 via the accessory processing unit 1101, and wireless communication 913 925 94. Data may also be logged to the user's smartphone over the same wireless connection 94.

Figure 10:
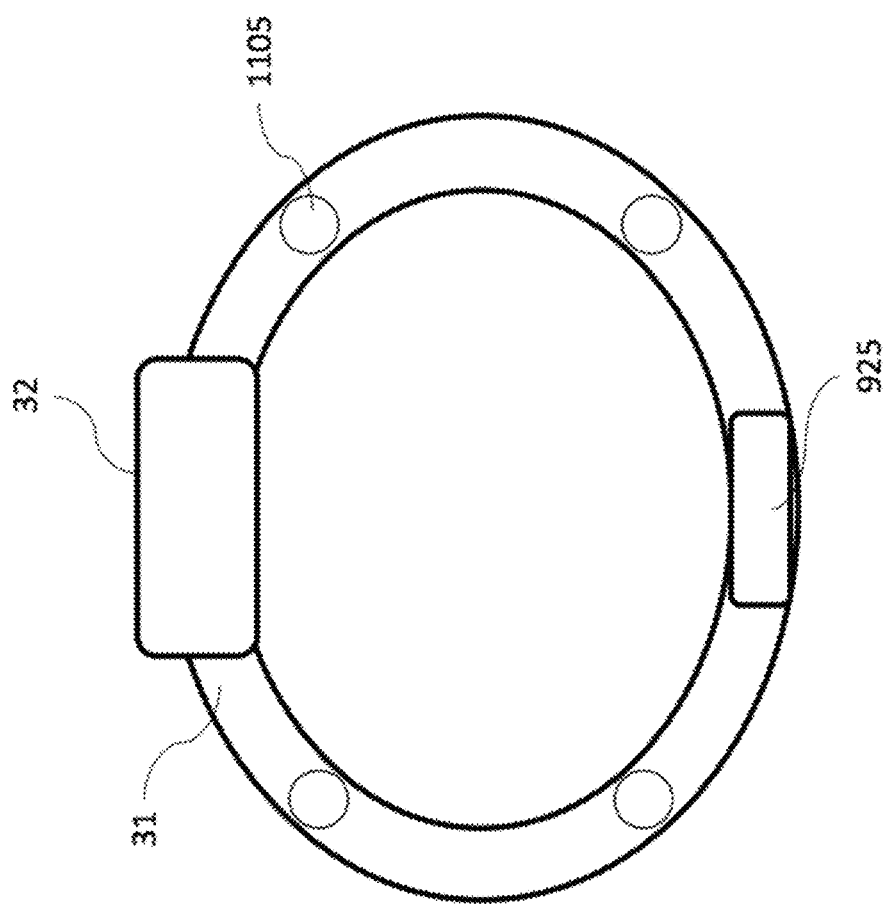
FIG. 10 shows a side view of a wearable device, which is as an accessory band for a third-party smartwatch or other wearable computing device, in accordance with an embodiment of the present invention.

FIG. 10 shows a side view of a wearable device, which is as an accessory band for a third-party smartwatch or other wearable computing device, in accordance with an embodiment of the present invention. It shows the main electronics housing 32 and the band 31 which contains the mechanical transducers 1105. The band 31 interfaces with the user's wrist. This view illustrates an example placement of the accessory battery 925 and processing unit 1101.

Figure 11:
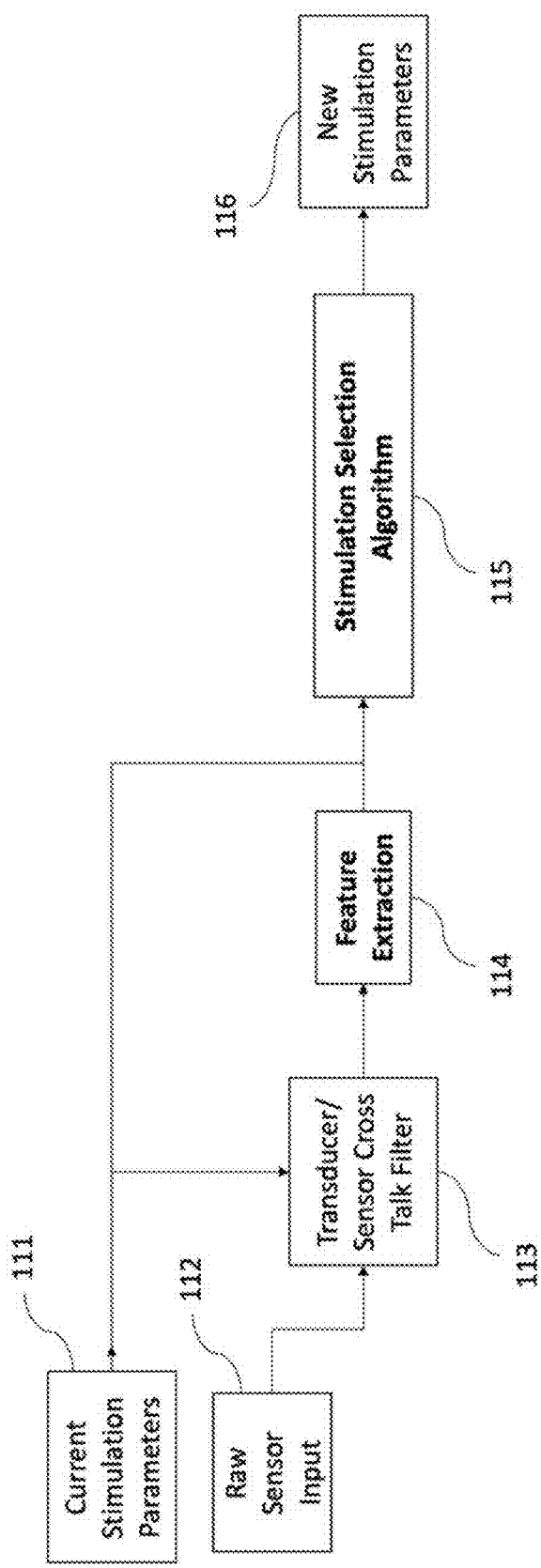
FIG. 11 shows a process by which a raw sensor input may be used to compute a set of stimulation parameters in accordance with an embodiment of the present invention.

FIG. 11 shows a process by which a raw sensor input may be used to compute a set of stimulation parameters in accordance with an embodiment of the present invention. The stimulation parameters are continuously updated in closed loop. These parameters can include any quantities used to define a stimulation waveform such as frequency, amplitude, phase, duty cycle, etc. At each iteration of the update loop, the current stimulation parameters 111 and raw sensor input 112 are used to filter out transducer/sensor crosstalk 113 either by using knowledge of the output waveform to subtract from the sensed waveform or by using knowledge of the timing of the output waveform to limit sensing to the "off" phases of a pulsing stimulation. This filtering subsequently allows for feature extraction 114 of the raw sensor input 112. The stimulation selection algorithm 115 then uses the current stimulation parameters 111 and the extracted features 114 to select new stimulation parameters 116. This process is illustrated in greater depth in FIG. 13. When the process repeats, the previously new stimulation parameters 116 become to the current stimulation parameters 111.

Figure 12:
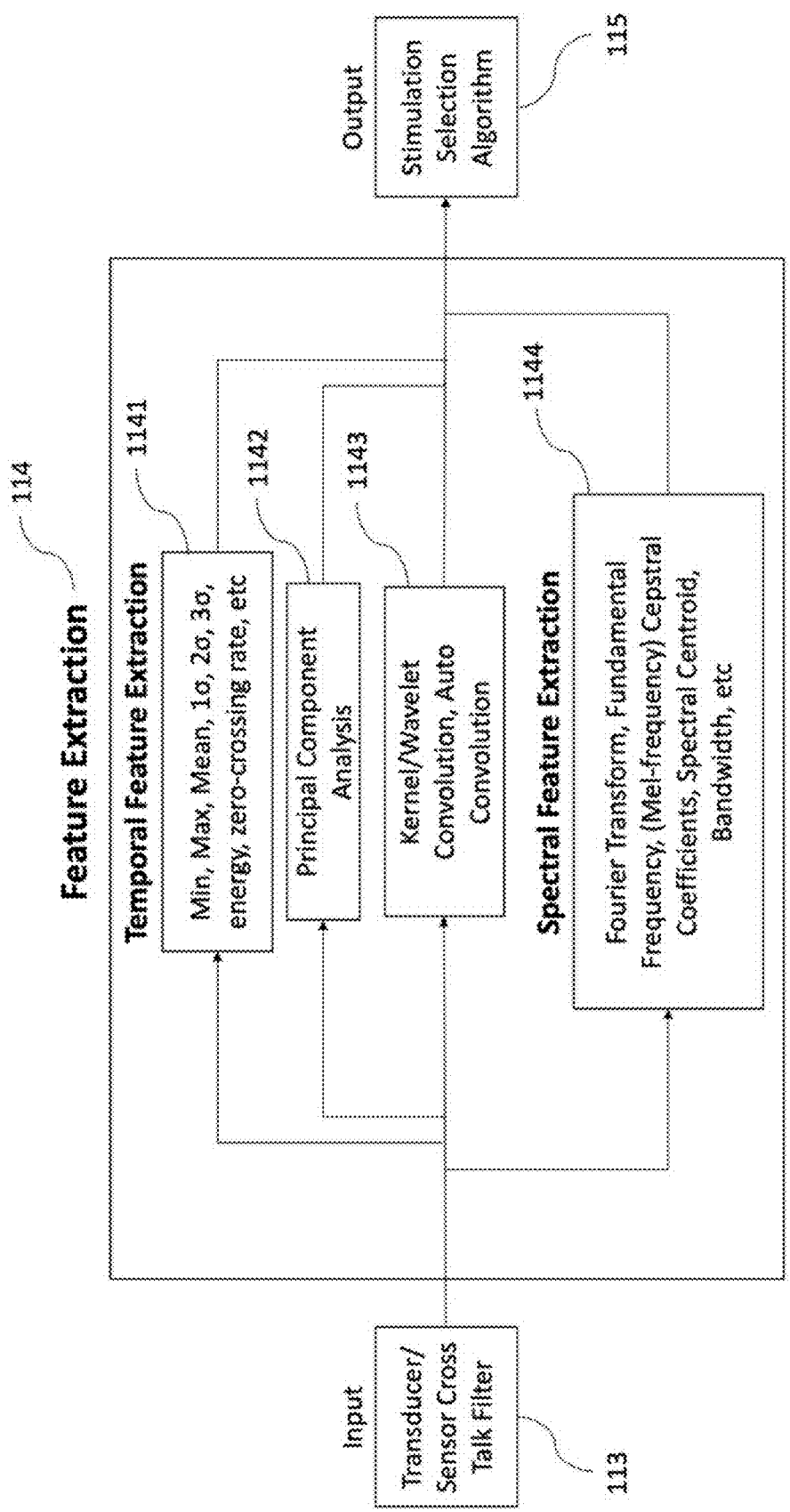
FIG. 12 shows a feature extraction process in accordance with an embodiment of the present invention.

FIG. 12 shows a feature extraction process in accordance with an embodiment of the present invention. This process takes in a filtered sensor signal, as described with respect to FIG. 11, and extracts temporal 1141 1142 1143 and/or spectral features 1144. Examples of common temporal features include the minimum value, the maximum value, first three standard deviation values, signal energy, root mean squared (RMS), zero crossing rate, principal component analysis (PCA), kernel or wavelet convolution, or autoconvolution. Examples of common spectral features include the Fourier Transform, fundamental frequency, (Mel-frequency) Cepstral coefficients, the spectral centroid, and bandwidth. Features are extracted with standard digital signal processing techniques onboard the main processing unit of the device. The set of collected features is then fed into the stimulation selection algorithm.

Figure 13:
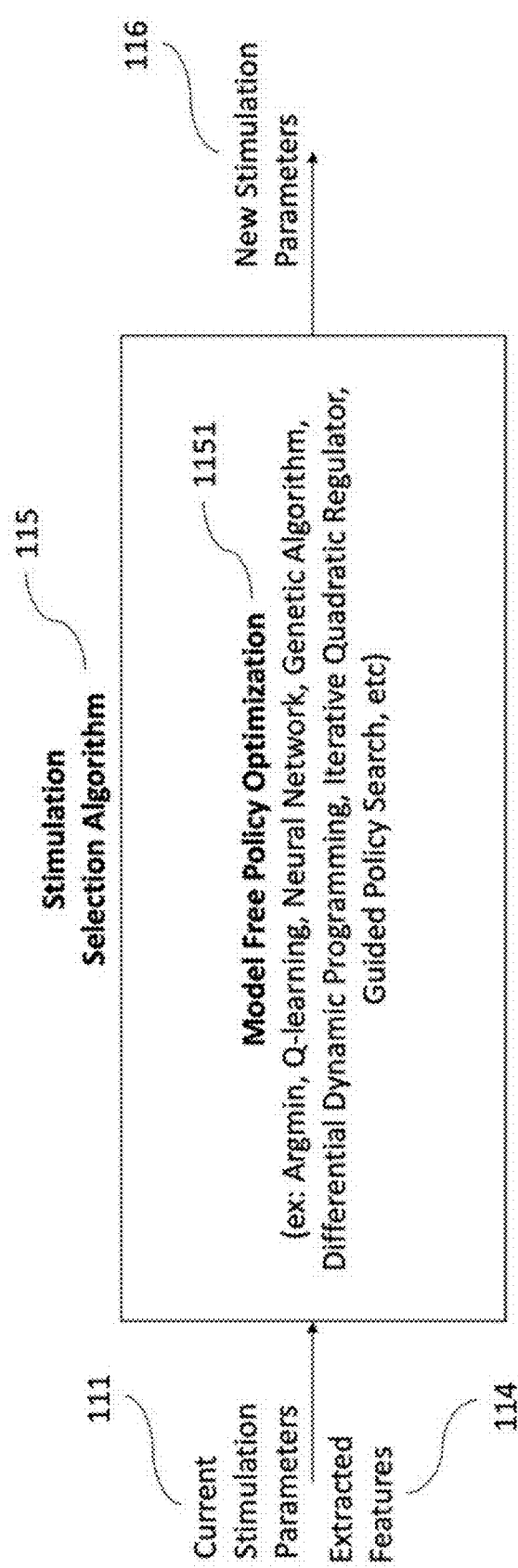
FIG. 13 shows a stimulation optimization algorithm in accordance with an embodiment the present invention.

FIG. 13 shows a stimulation optimization algorithm in accordance with an embodiment the present invention. The stimulation selection algorithm takes in the extracted features 114 and the current stimulation parameters 111 and uses them to determine the set of new stimulation parameters 116. The process by which the new parameters are determined is an optimization to minimize the symptom severity. Given that there is no analytical model for the symptom's response to stimulation patterns, this optimization is inherently model free. Examples of model free policy optimization techniques are argmin (or minimization over the set of input arguments), Q-learning, neural networks, genetic algorithms, differential dynamic programming, iterative quadratic regulator, and guided policy search. Descriptions of some such algorithms can be found in Deisenroth, M. P. (2011), "A Survey on Policy Search for Robotics," *Foundations and Trends in Robotics*, 2(1-2), 1-142. doi:10.1561/2300000021; and Beasley, D., Bull, D. R., & Martin, R. (1993), "An Overview of Genetic Algorithms: Part 1, Fundamentals," 1-8, (herein incorporated, in their entirety, by reference).

In an example, an extracted feature may be the amplitude of the tremor and the set of current stimulation parameters could be a stimulation frequency and amplitude. A stimulation selection algorithm can then compare the tremor amplitude observed with the current set of stimulation parameters to the tremor amplitude observed with a previous set of stimulation parameters to determine which of the two sets of stimulation parameters resulted in the lowest tremor amplitude. The set with the lowest resulting tremor amplitude could then be used as the baseline for the next iteration of the stimulation selection algorithm which would compare it to a new set.

Two example stimulation selection algorithm that may be used in embodiments follow:

---
Algorithm 1 Determine Optimal Vibration Motor State
---

Input: Feed of x,y,z accelerometer data
Output: Output state which minimizes tremor magnitude
    1: AmplitudeStates = $\{A_1, A_2, ..., A_n\} = \{A\}_n$
    2: FrequencyStates = $\{F_1, F_2, ..., F_m\} = \{F\}_m$
    3: OutputStates = $\{A \times F\}_{n \times m}$
    4: TremorResponses = $\{0\}_{n \times m}$
    5:
    6: for State in OutputStates do
    7: Output←State
    8: TremorResponses[State]←ReadAccelerometer 9: OptimalState ← $\underset{\{A\},\{F\}}{\mathrm{argmin}}$ TremorResponses ---
Algorithm 2 Q-learning Algorithm
---

Input: Feed of x,y,z accelerometer data
Output: Output state which minimizes tremor magnitude
    1: AmplitudeStates = $\{A_1, A_2, ..., A_n\} = \{A\}_n$
    2: FrequencyStates = $\{F_1, F_2, ..., F_m\} = \{F\}_m$
    3: OutputStates = $\{A \times F\}_{n \times m} = S$
    4: Choices = {IncreaseAmplitude, IncreaseFrequency} = C
    5: QTable = $Q : S \times C \to \mathbb{R}$
    6: for Epoch in MaxEpochs do
    7: for s in OutputStates do
    8: for e in Choices do 9:   r ← ReadAccelerometer
   10:
   11:

$$Q(s, c) \leftarrow (1 - \alpha) \cdot Q(s, c) + \alpha \cdot \left(r + \gamma \cdot \min_{k \in C} Q(s+1, k)\right)$$

OptimalState ← $\underset{s}{\mathrm{argmin}}$ Q

In some embodiments, the structure of the output stimulation pattern may be a weighted average of optimized patterns corresponding to each symptom where the weights are proportional to the symptom severity relative to the other observed symptoms. In some embodiments, the structure of the output stimulation pattern may just be the pattern optimized to reduce the most severe symptom.

Figure 14:
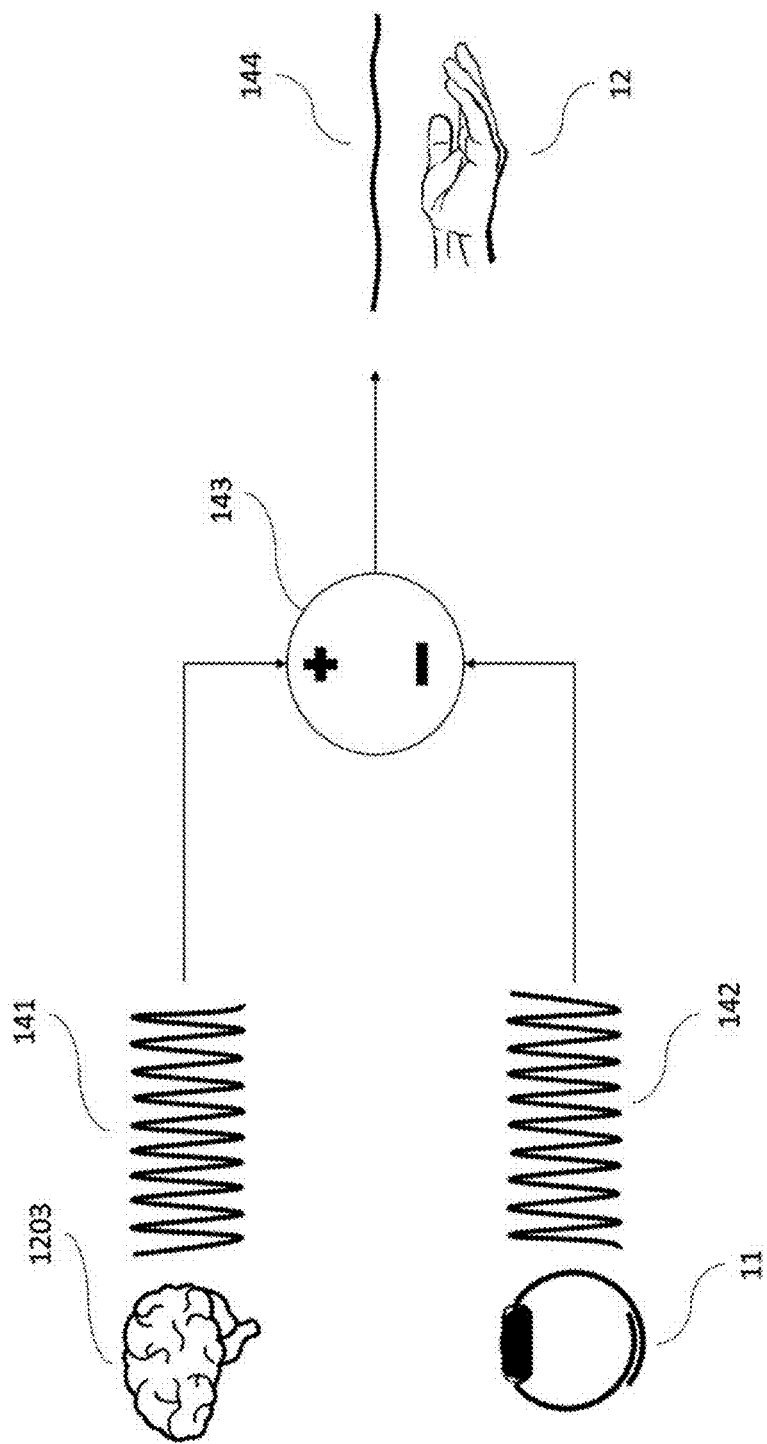
FIG. 14 shows a neurological signal cancelling system, illustrating how the wearable device and body interact, in accordance with an embodiment of the present invention.

FIG. 14 shows a neurological signal cancelling system, illustrating how the wearable 11 device and body 12 interact, in accordance with an embodiment of the present invention. The system comprises of the user's nervous system 1203, which sends control signals 141 to the body 12. The wearable 11 senses the body's movement and sends an opposing control signal which is defined by the output of the stimulation parameter selection algorithm. 142. The control signals undergo a signal cancelling process within the nervous system of the user 143, which results in a smoother perceived motion signal 143.

Figure 15:
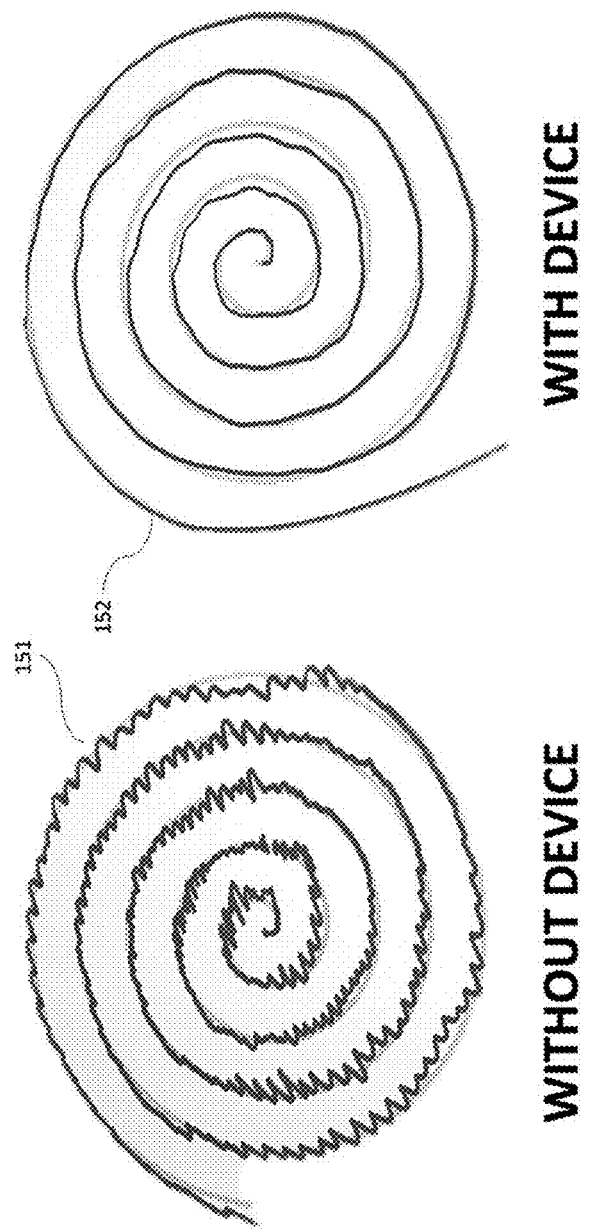
FIG. 15 is a pair of renderings by a Parkinson's patient of a spiral under conditions without and with treatment by a device in accordance with an embodiment of the present invention.

FIG. 15 is a pair of renderings 151 152 by a tremor patient of an Archimedes spiral under conditions without and with treatment by a device in accordance with an embodiment of the present invention. The spiral tracing test allows doctors to gain insight on the frequency, amplitude, and direction of their patients' tremors. It can also inform the doctor of abnormal movement of hypokinesia, dystonia, and tremor. The task requires the patient to continuously trace the Archimedes spiral. Patients who have tremors will have difficulty following the spiral and will trace off the spiral line resulting in a disordered spiral 151. Wearing a device in accordance with an embodiment of the present invention, the patient is able to trace the spiral more accurately resulting in a smoother spiral 152.

Figure 16:
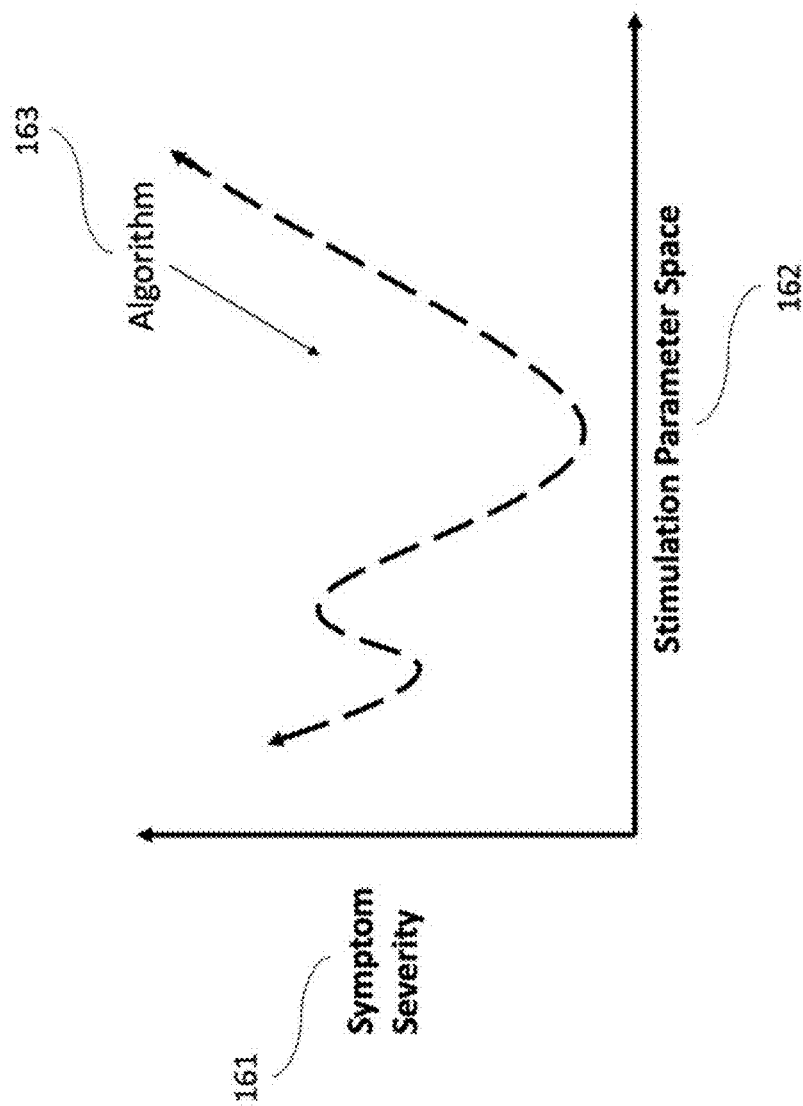
FIG. 16 illustrates an embodiment of a simple non-convex gradient descent optimization used in embodiment of the present invention for symptom reduction by searching over the parameter configuration space.

FIG. 16 illustrates an embodiment of a simple non-convex gradient descent optimization used in embodiment of the present invention for symptom reduction by searching over the parameter configuration space. It is a graphical representation of the stimulation selection algorithm 163 associated with the present invention. The algorithm 163 moves through the stimulation parameter space 162 and attempts to minimize symptom severity 161. The movement through the stimulation parameter space can be thought of as trying different sets of stimulation parameters and comparing their resulting symptom severities as quantified by their respective sensors. The algorithm attempts to minimize symptom severity by testing different sets of parameters until an optimal set for minimizing symptom severity is found.

Alternative benchtop versions of the device can be used to elicit tremors in Parkinson's patients for the purposes of early detection. This is done using the same mechanisms as in reducing tremor but using an inverted stimulation parameter search heuristic. User testing has shown that for each patient, there exists a stimulation pattern which when applied to the Parkinson's patient with very slight tremor will produce a very large tremor. This effect does not occur in users who do not have Parkinson's Disease. This could be used for earlier detection and diagnosis of Parkinson's Disease which can be difficult to diagnose.

Figure 17:
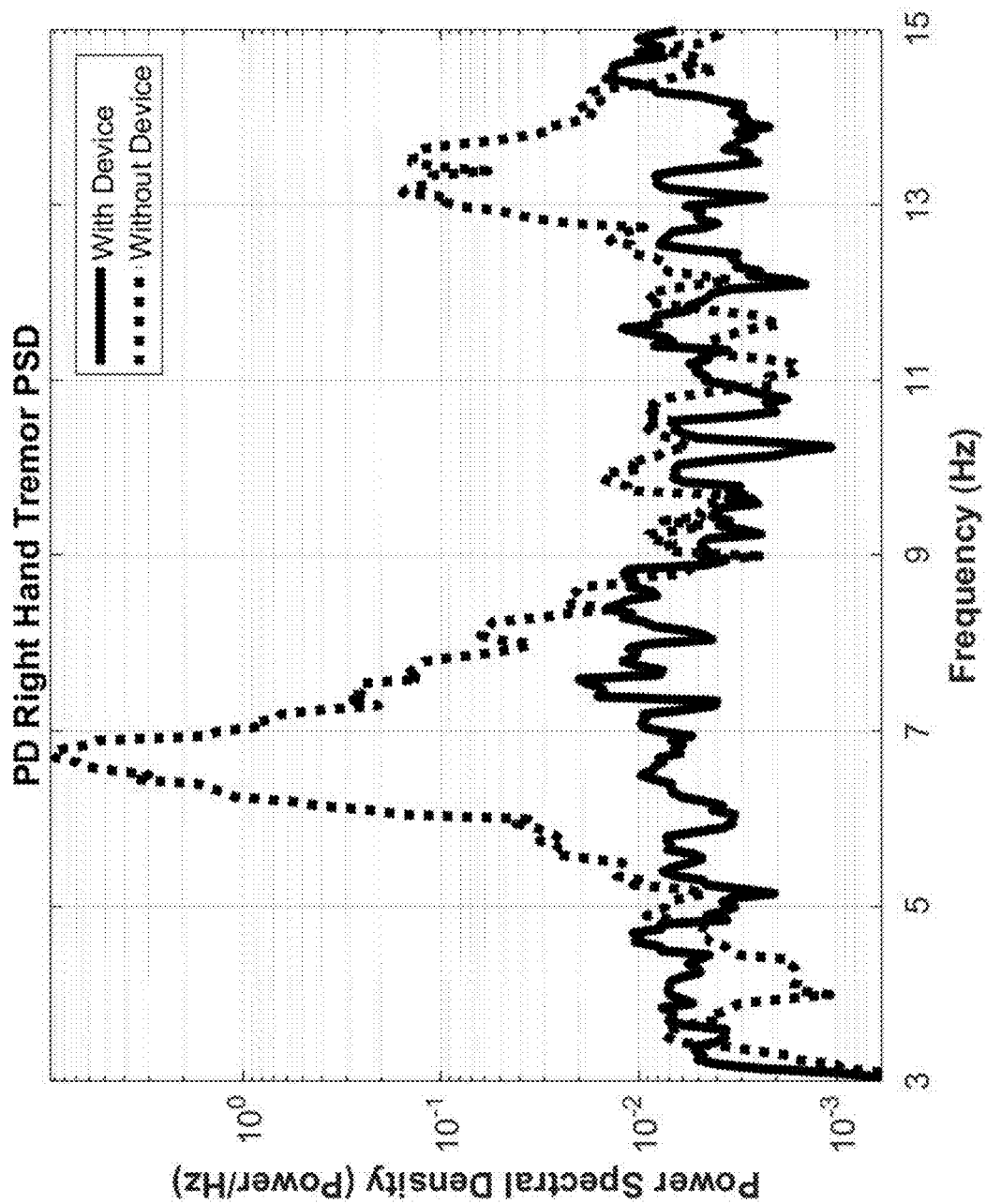
FIG. 17 shows a power spectral density (PSD) plot of the postural tremor of a Parkinson's Disease patient with and without the use of a device in accordance with an embodiment of the present invention.
Figure 18:
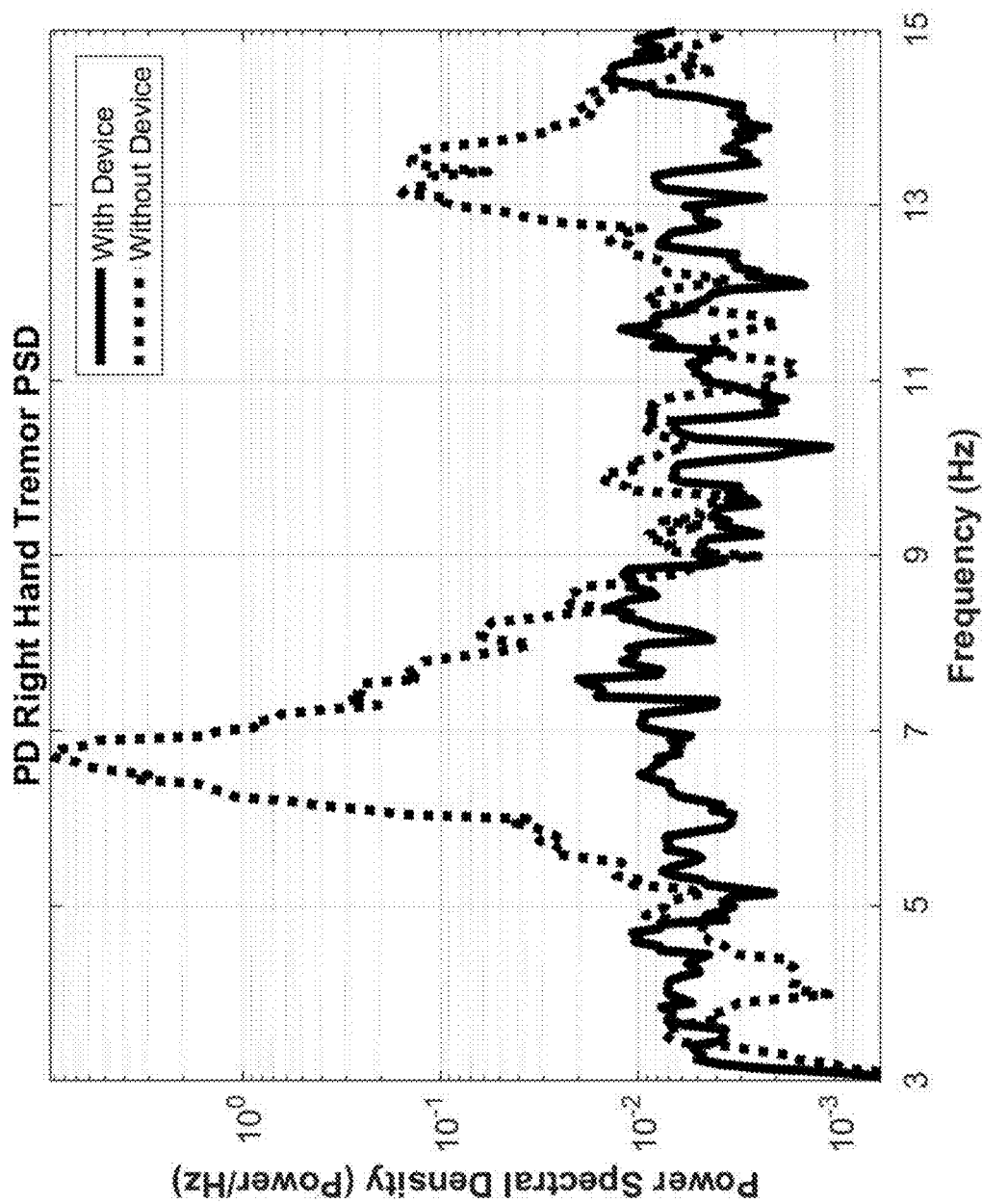
FIG. 18 shows a power spectral density (PSD) plot of the postural tremor of an Essential Tremor patient with and without the use of a device in accordance with an embodiment of the present invention.

FIGS. 17 and 18 each shows a power spectral density (PSD) plot of the postural tremor of a Parkinson's Disease and Essential Tremor patient, respectively, with and without the use of a device in accordance with an embodiment of the present invention. The data was taken by asking each patient to hold his or her hand out for 10 seconds, with and without the device. In FIGS. 17 and 18, tremor amplitude is compared with and without the device.

The following describes a test case of an embodiment of the present invention. Participants were asked to trace a printed Archimedes Spiral, a common test used to diagnose Parkinson's, with and without the device, as shown in FIG. 15. The results were measured by using image processing software to evaluate the accuracy of the traced spirals. In the first round of testing, the device was tested on around 20 participants with Parkinson's and 1 participant with a resting tremor. The majority of the participants, however, either did not experience tremors or were already being treated for Parkinson's and only experienced slight tremors. It was observed that the reduction in tremor severity was strongly correlated to the initial tremor severity. That is, patients with minimal tremors experienced minimal benefit while patients with more extreme tremors experienced more dramatic benefit. The participant with the most severe resting tremor, caused by Parkinson's Disease, saw the most improvement in performance as shown in FIG. 17. Another participant with a resting tremor, caused by Essential Tremor, also showed significant improvement as shown in FIG. 18. The results were repeatable with both of these participants. Participants who suffered from rigidity observed that they had a larger range of movement in their hands and completed their spiral tests faster with the device than without.

While the above embodiments reference accelerometers, vibration motors, microUSB, and wristbands the invention is not limited to such implementations. Additionally, the above embodiments are not intended to limit the scope of the invention. For example, various modifications and variations of interfaces, types of electromyography sensors, gyroscopes, inertial measurement units, piezoelectrics, electromagnets, electropermanent magnets, pneumatics, voice coils, hydraulics, resistive heating elements should be included. The scope of form factors should also include headbands, collars, anklets, armbands, and rings. The scope of electrical interfaces should include Thunderbolt cables, USB, USB C, microUSB, wireless communication, wireless charging, and Bluetooth communication.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A wearable device for mitigating a movement disorder of a subject, the device comprising:
   a. a set of body part sensors, configured to be attached to a body part of the subject, to provide a set of sensor outputs related to involuntary movement of the body part attributable to the movement disorder;
   b. a processing unit operationally coupled to the set of body part sensors and configured to quantify frequencies and amplitudes of the involuntary movement associated with the movement disorder measured by the set of sensor outputs;
   c. a set of vibration motors configured to be attached to the body part of the subject, operationally coupled to the processing unit to provide a set of vibrational outputs to provide vibrational stimulation to proprioceptive nerves of the body part;
   wherein the processing unit is further configured, as part of a feedback loop including the body part sensors, the vibration motors, and the body part, to adjust parameters of the vibrational stimulation to the proprioceptive nerves of the body part utilizing a stimulation selection algorithm, wherein the stimulation selection algorithm receives extracted features of the sensor outputs and current stimulation parameters of the vibrational stimulation and determines a new set of stimulation parameters of the vibrational stimulation based on the extracted features and the current stimulation parameters; and wherein the processing unit is further configured to filter out sensor crosstalk by limiting sensing of the at least a sensor to off phases of the vibrational stimulation.

2. The wearable device of claim 1, wherein the movement disorder has symptoms selected from the group consisting of tremor, rigidity, bradykinesia, compulsion to move, and combinations thereof.

3. The wearable device of claim 1, wherein the processing unit is further configured to detect a freezing gait of a patient with Parkinson's Disease.

4. The wearable device of claim 3, wherein the processing unit is further configured to control the set of vibration motors so as to relieve the freezing gait of a patient with Parkinson's Disease.

5. The wearable device of claim 1, wherein the device is configured to be fully autonomous, using passive movement disorder sensing to initiate active operation.

6. The wearable device of claim 1, wherein the processing unit is further configured to control the vibration motors, without requiring control inputs from external control units.

7. The wearable device of claim 1, wherein the processing unit is further configured to collect and store data.

8. The wearable device of claim 1, wherein the processing unit is configured to adjust parameters of the vibrational stimulation by means of sensor-based optimization selected from the group consisting of model free reinforcement learning, genetic algorithms, and Q-learning.

9. A system for a wearable device for mitigating a movement disorder of a subject, comprising:
   at least a sensor configured to be attached to the subject, wherein the at least a sensor generates a sensor output related to involuntary movement of the subject;
   a processing unit in communication with the at least a sensor, wherein the processing unit is configured to receive the sensor output and generate a vibrational stimulation based on the sensor output;
   at least a vibration motor configured to be attached to the subject and in communication with the processing unit, wherein the at least a vibration motor is configured to provide vibrational outputs of the vibrational stimulation to a body part of the subject; and
   wherein the processing unit is further configured to: receive sensor input from the at least a sensor; filter out sensor crosstalk of the sensor input by subtracting an output waveform of the vibrational stimulation from a sensed waveform of the sensor input; and wherein the processing unit is further configured to filter out sensor crosstalk by limiting sensing of the at least a sensor to off phases of the vibrational stimulation.

10. The system of claim 9, wherein the extracted features include temporal features of the sensed waveform.

11. The system of claim 9, wherein the extracted features include spectral features of the sensed waveform.

12. The system of claim 9, wherein the processing unit is further configured to select new stimulation parameters based on the extracted features and current stimulation parameters of the vibrational stimulation.

13. The system of claim 9, wherein the processing unit is further configured to:
   perform feature extraction of the filtered sensor output to generate extracted features of the sensed waveform; and select new stimulation parameters based on the extracted features from the filtered sensor output.

* * * * *